United States Patent
Emmett et al.

(10) Patent No.: US 10,875,846 B2
(45) Date of Patent: Dec. 29, 2020

(54) PROCESSES FOR THE PREPARATION OF TEZACAFTOR AND INTERMEDIATES THEREOF

(71) Applicant: Apotex Inc., Toronto (CA)

(72) Inventors: Michael R. Emmett, Delaware (CA); Prabhudas Bodhuri, San Ramon, CA (US); Yajun Zhao, Brantford (CA); Eduardo Gustavo Cammisa, Markham (CA); Stuart P. Green, Mount Pleasant (CA)

(73) Assignee: Apotex Inc., Toronto (CA)

( * ) Notice: Subject to any disclaimer, the term of this patent is extended or adjusted under 35 U.S.C. 154(b) by 0 days.

(21) Appl. No.: 16/741,276

(22) Filed: Jan. 13, 2020

(65) Prior Publication Data

US 2020/0223832 A1    Jul. 16, 2020

Related U.S. Application Data

(60) Provisional application No. 62/792,543, filed on Jan. 15, 2019.

(51) Int. Cl.
| | | |
|---|---|---|
| *C07D 405/12* | (2006.01) | |
| *C07C 211/52* | (2006.01) | |
| *C07D 317/60* | (2006.01) | |

(52) U.S. Cl.
CPC .......... *C07D 405/12* (2013.01); *C07C 211/52* (2013.01); *C07D 317/60* (2013.01)

(58) Field of Classification Search
CPC .... C07D 405/12; C07D 317/60; C07C 211/52
See application file for complete search history.

(56) References Cited

U.S. PATENT DOCUMENTS

| | | | |
|---|---|---|---|
| 8,563,593 | B2 | 10/2013 | Alargova et al. |
| 10,071,979 | B2 | 9/2018 | Tanoury et al. |
| 10,206,877 | B2 | 2/2019 | Phenix et al. |
| 2009/0131492 | A1 | 5/2009 | Ruah et al. |
| 2011/0251253 | A1 | 10/2011 | Keshavarz-Shokri et al. |
| 2012/0046330 | A1 | 2/2012 | Alargova et al. |
| 2013/0131107 | A1 | 5/2013 | Van Goor et al. |
| 2013/0143919 | A1 | 6/2013 | Van Goor et al. |
| 2013/0159071 | A1 | 6/2013 | Inks |
| 2015/0080431 | A1 | 3/2015 | Van Goor et al. |

FOREIGN PATENT DOCUMENTS

| | | |
|---|---|---|
| WO | 2011119984 A1 | 9/2011 |
| WO | 2011133751 A2 | 10/2011 |
| WO | 2011133951 A1 | 10/2011 |
| WO | 2011133953 A1 | 10/2011 |
| WO | 2011133956 A1 | 10/2011 |
| WO | 2012027247 A2 | 3/2012 |
| WO | 2012170061 A1 | 12/2012 |
| WO | 2013185112 A1 | 12/2013 |
| WO | 2015160787 A1 | 10/2015 |

*Primary Examiner* — Shawquia Jackson
(74) *Attorney, Agent, or Firm* — The Webb Law Firm

(57) ABSTRACT

The present invention provides processes for the preparation of Tezacaftor, as well as intermediates useful in the preparation thereof. In particular, processes are provided for the preparation of a compound of Formula (3), and its conversion to Tezacaftor (1).

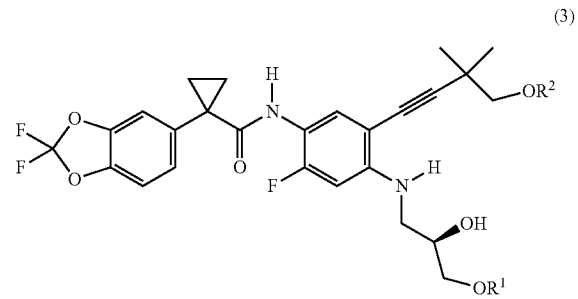

(3)

20 Claims, No Drawings

PROCESSES FOR THE PREPARATION OF TEZACAFTOR AND INTERMEDIATES THEREOF

CROSS-REFERENCE TO RELATED APPLICATION

This application claims the benefit of U.S. Provisional Patent Application No. 62/792,543, filed Jan. 15, 2019, the disclosure of which is hereby incorporated in its entirety by reference.

TECHNICAL FIELD

The present invention relates to processes for the preparation of Tezacaftor and intermediates used in the preparation thereof.

BACKGROUND

Tezacaftor (1), or 1-(2,2-difluoro-2H-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropane-1-carboxamide, is one of the active ingredients in SYMDEKO®, which is provided as a co-packaged Tezacaftor/Ivacaftor fixed-dose combination tablet and an Ivacaftor tablet. SYMDEKO® is indicated for the treatment of patients with cystic fibrosis (CF) aged 12 years and older who are homozygous for the F508del mutation, or who have at least one mutation in the cystic fibrosis transmembrane conductance regulator (CFTR) gene that is responsive to Tezacaftor/Ivacaftor based on in vitro data and/or clinical evidence.

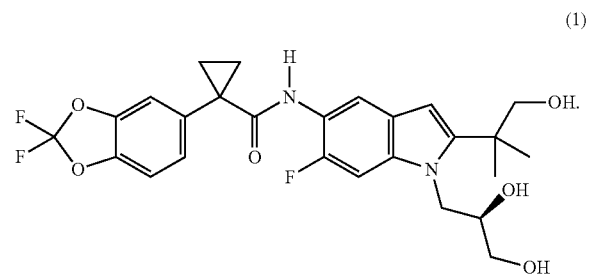 [SMILES: CC(C)(CO)c1cc2cc(NC(=O)C3(c4ccc5c(c4)OC(F)(F)O5)CC3)c(F)cc2n1C[C@@H](O)CO]

(1)

One process of preparing Tezacaftor (1) is described in US 2009/0131492 A1, which discloses a family of compounds that are stated to be useful as modulators of ATP-Binding Cassette ("ABC") transporters or fragments thereof, including Cystic Fibrosis Transmembrane Conductance Regulator ("CFTR"). In this process, which is depicted in Scheme 1, Tezacaftor (1) is prepared by amide coupling of amino indole (H) with difluorobenzodioxol carbonyl chloride (I) to form the compound of Formula (J), followed by deprotection of the acetonide-protected diol chain. The indole ring of amino indole (H) is prepared by palladium-mediated cyclization of intermediate (C), formed via a Sonogashira coupling of aryl bromide (A) and butynyl ester (B), to provide intermediate (D). Following alkylation of intermediate (D), the resulting mixture comprising compounds (F1) and (F2) is reduced to provide alcohol (G), which then undergoes nitro reduction to provide the intermediate (H).

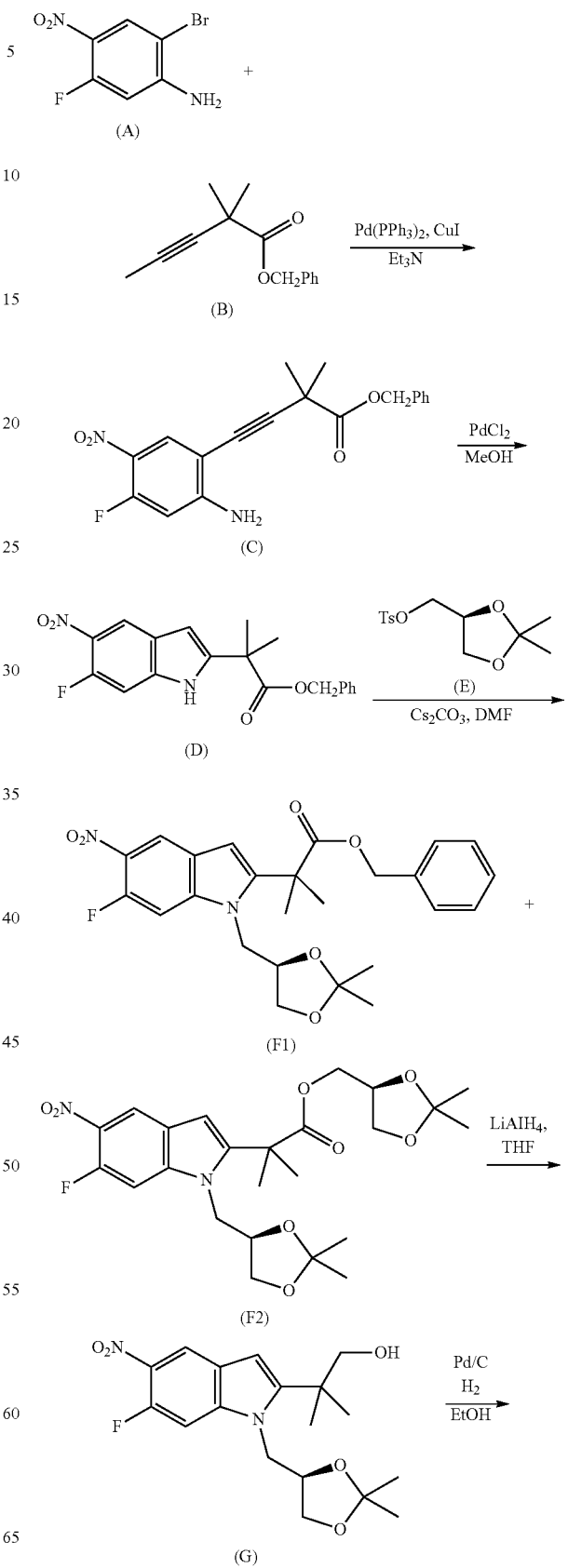

Scheme 1 (Prior Art)

-continued

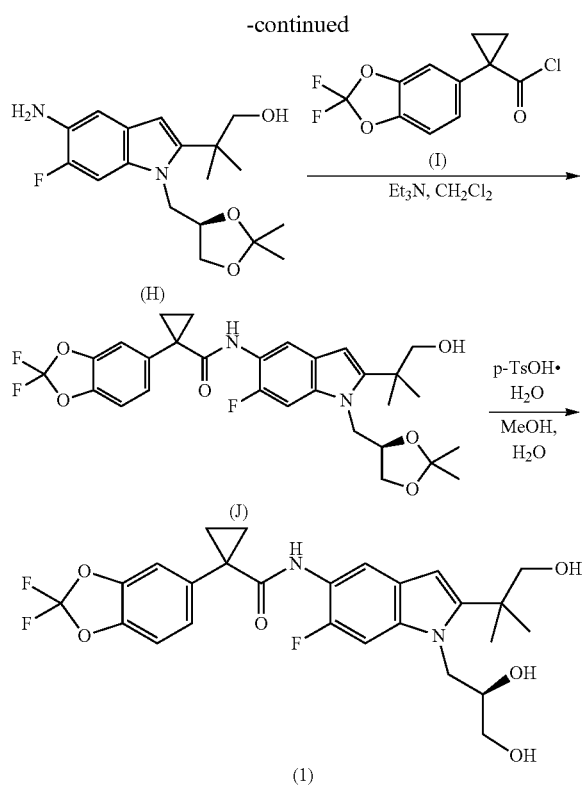

This process has significant drawbacks, including the extensive use of column chromatography for the purification of Tezacaftor and the intermediates thereof, and a low overall yield of around 16%.

A second process for the preparation of Tezacaftor (1) is described in WO 2011/133751 A2. In this process, which is exemplified in Scheme 2, the final steps are similar to the process described in US 2009/0131492 A1, involving amide coupling of an amino indole (Q) with difluorobenzodioxol carbonyl chloride (I), followed by deprotection of the resulting dibenzyl-protected compound (R) to afford Tezacaftor (1). Like the process described in US 2009/0131492 A1, the indole ring of intermediate (Q) is formed by Sonogashira coupling, followed by palladium-mediated cyclization. However, in the process described in WO 2011/133751 A2, the aryl bromide substrate (M) bears a benzyl-protected sidechain from alkylation of starting material (A) with epoxide (K), and the nitro group of intermediate (L) has been reduced to an amino group. Further, the butynyl compound (O) bears a benzyl ether rather than a benzyl ester group.

Similar processes involving the same synthetic route used for the second process are disclosed in WO 2011/119984 A1, WO 2011/133951 A1, WO 2011/133953 A1, WO 2011/133956 A1, WO 2012/170061 A1, WO 2012/027247 A2, WO 2013/185112 A1 and WO 2015/160787 A1.

A problem with this second process to prepare Tezacaftor (1) is the prevalence of intermediates obtained as oils and residues, which complicates handling and purification during commercial-scale manufacturing. As such, the second process, which is depicted in Scheme 2, comprises several telescoped steps wherein compounds are not isolated, but rather, carried through directly to the subsequent step. While this process can afford process efficiencies, the lack of crystallizable solids provides little opportunity for the control of impurities at different stages of the process, which leads to a large purification burden in the steps that do afford a solid. For example, in the eight-step process from compound (A) to Tezacaftor (1), there are only three isolatable solids: intermediates (N) and (Q), and Tezacaftor (1). Furthermore, although yields are not reported for the first four steps, the remaining steps afford Tezacaftor in an overall yield of only 18-32%.

Scheme 2 (Prior Art)

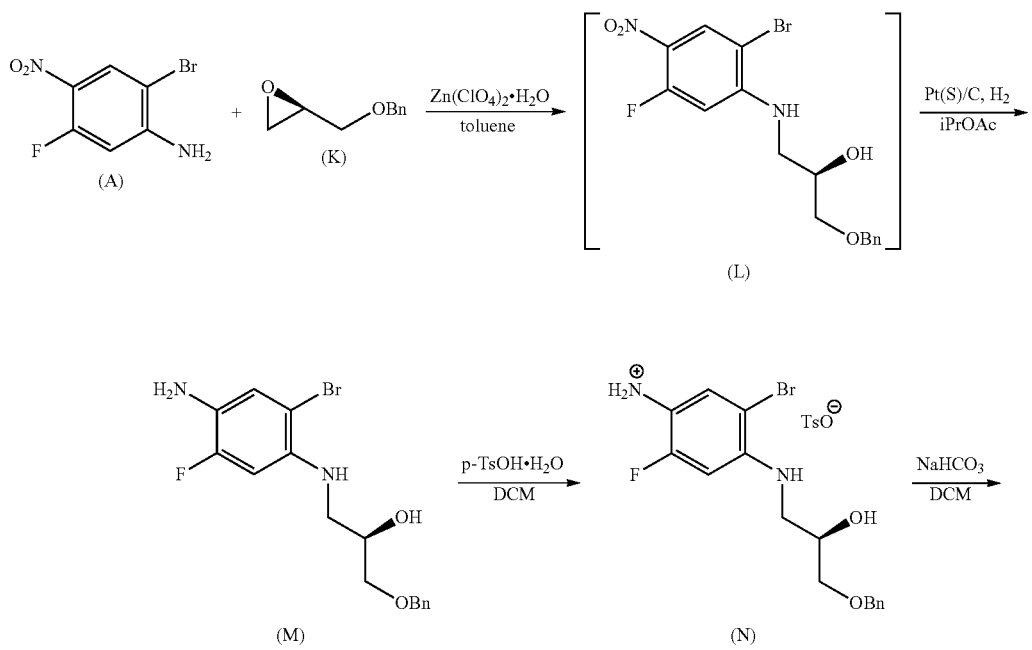

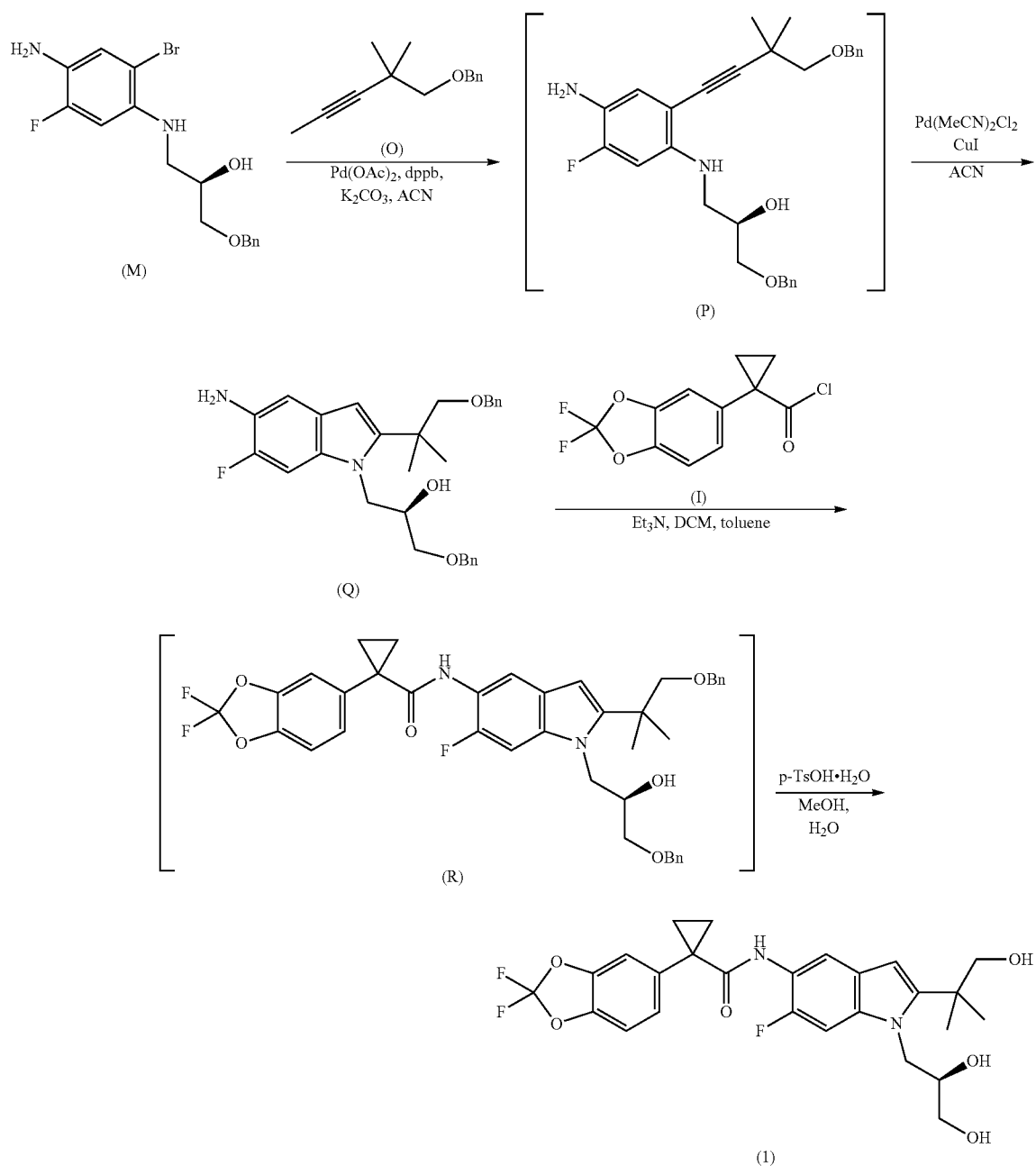

Owing to the drawbacks of the existing processes, there remains a need for improved processes for the preparation of Tezacaftor (1), and the intermediates used in such preparations, that are more amenable to scale-up and use on a commercial scale.

SUMMARY OF THE INVENTION

The present invention provides improved processes for the preparation of Tezacaftor (1), as well as new intermediates and processes for the preparation thereof, as depicted in Scheme 3.

As shown in Scheme 3, in the processes of the present invention, Tezacaftor (1) is prepared by indolization of the compound of Formula (3), bearing the difluorobenzodioxol ring, to afford either Tezacaftor (1) or the intermediate of Formula (2), which can be further reacted to provide Tezacaftor (1). The difluorobenzodioxol ring of the compound of Formula (3) may be introduced by coupling of the compound of Formula (9) with the compound of Formula (10), the latter compound formed from sequential protection and reduction of the compounds of Formula (12) and (11), respectively. Following deprotection of the compound of Formula (8), the resulting compound of Formula (7) may be coupled with the compound of Formula (6) to afford the compound of Formula (5), which undergoes Sonogashira-type coupling with the compound of Formula (4) to afford the compound of Formula (3).

Scheme 3
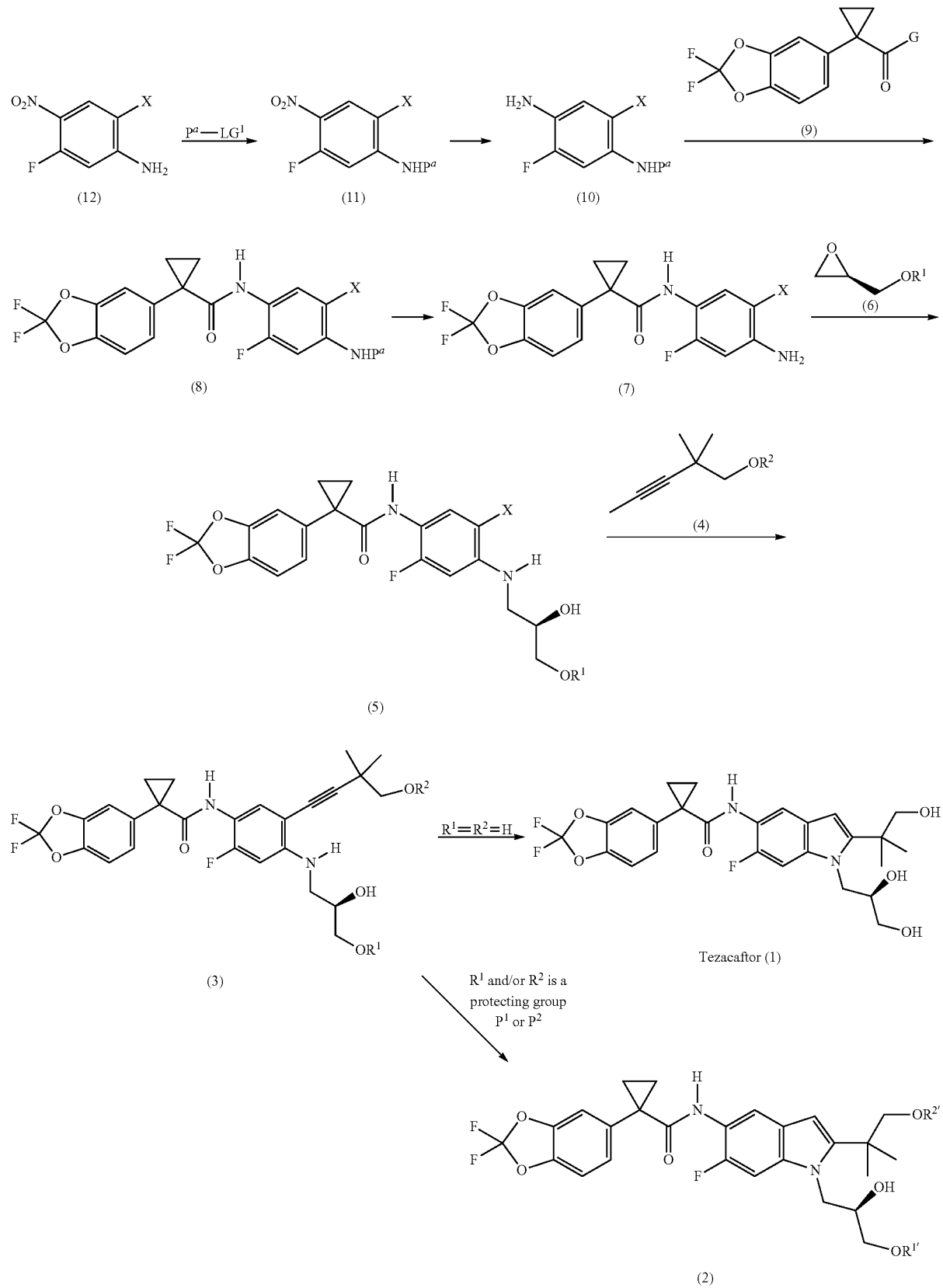

wherein
X is halide or trifluoromethanesulfonate;
G is OH or $LG^2$;
$LG^1$ and $LG^2$ are leaving groups that may be the same or different;
$R^1$ is H or $P^1$;
$R^2$ is H or $P^2$;
$R^{1'}$ is H or $P^1$;
$R^{2'}$ is H or $P^2$;
$R^{1'}$ and $R^{2'}$ are not both H;
$P^a$ is an amino protecting group; and
$P^1$ and $P^2$ are hydroxyl protecting groups;

The processes of the present invention are practical and industrially applicable, with most reactions occurring at ambient temperature in good yield and providing isolatable solid products. Accordingly, the processes of the present invention provide important advantages that are applicable to the commercial preparation of Tezacaftor (1).

Accordingly, in a first aspect of the present invention, there is provided a process for the preparation of Tezacaftor (1), comprising:
(i) cyclizing, in the presence of a catalyst (C3) and a solvent (S7), a compound of Formula (3), or a salt thereof, to provide either Tezacaftor (1) when each of $R^1$ and $R^2$ in the compound of Formula (3) is H, or, when either or both of $R^1$ and $R^2$ in the compound of Formula (3) is a respective hydroxyl protecting group $P^1$ or $P^2$, a compound of Formula (2), or a salt thereof, and
(ii) when either or both of $R^1$ and $R^2$ in the compound of Formula (3) is a respective hydroxyl protecting group $P^1$ or $P^2$, deprotecting, in the presence of a solvent (S8), the compound of Formula (2) to provide Tezacaftor (1).

In a preferred embodiment of the first aspect, catalyst (C3) is selected from the group consisting of tetrakis(triphenylphosphine)palladium(0), palladium(II) chloride, palladium(II) iodide, bis(benzonitrile)palladium(II) dichloride, bis(triphenylphosphine)palladium(II) dichloride, bis(acetonitrile)palladium(II) dichloride, palladium(II) trifluoroacetate, copper(II) acetate and indium(III) bromide. Most preferably, the catalyst (C3) is palladium(II) chloride.

In another preferred embodiment of the first aspect, solvent (S7) is selected from the group consisting of tetrahydrofuran, ethanol, isopropanol, N,N-dimethylformamide, N-methyl-2-pyrrolidinone, toluene and acetonitrile.

In another preferred embodiment of the first aspect, $R^1$ is $P^1$, $R^2$ is $P^2$, and $P^1$ and $P^2$ are $CR^aR^bR^c$ groups that may be the same or different in the compound of Formula (3). $R^a$, $R^b$ and $R^c$ are independently selected from the group consisting of H, an alkyl group having 1 to 10 carbon atoms, a substituted alkyl group having 1 to 10 carbon atoms in the alkyl portion, an unsubstituted aryl group having 6 to 14 ring carbon atoms, and a substituted aryl group having 6 to 14 ring carbon atoms; and at least one of the groups $R^a$, $R^b$ and $R^c$ is a substituted or unsubstituted aryl group having 6 to 14 ring carbon atoms. Preferably, each of $P^1$ and $P^2$ is a benzyl group.

In a further preferred embodiment of the first aspect, deprotecting the compound of Formula (2) comprises hydrogenation in the presence of a catalyst (C4) selected from the group consisting of palladium, platinum, rhodium, ruthenium, and Raney-nickel. Preferably, catalyst (C4) is palladium on carbon.

In another preferred embodiment of the first aspect, solvent (S8) is selected from the group consisting of methanol, ethanol, isopropanol, tetrahydrofuran and dioxane. Preferably, solvent (S8) is methanol.

In a further preferred embodiment of the first aspect, the compound of Formula (3), or a salt thereof, is prepared by reacting, in the presence of a catalyst (C2), a solvent (S6) and a base (B2), a compound of Formula (5), or a salt thereof, with a compound of Formula (4).

Within this preferred embodiment of the first aspect, catalyst (C2) is selected from the group consisting of [1,1'-bis(diphenylphosphino)ferrocene]dichloropalladium(II), [1,1'-bis(di-tert-butylphoshino)ferrocene]dichloropalladium (I), tetrakis(triphenylphosphine)palladium(0), bromo(tri-tert-butylphosphine)palladium(I) dimer, bis(tri-tert-butylphosphine)palladium(0), palladium(II) acetate, palladium(II) chloride, bis(benzonitrile)palladium(II) dichloride, bis(triphenylphosphine)palladium(II) dichloride, bis(acetonitrile)palladium(II) dichloride, bis[di-tert-butyl(4-dimethylaminophenyl)phosphine]dichloropalladium(II), bis [di-tert-butyl(4-dimethylaminophenyl)phosphine]palladium (0) and allylpalladium(II) chloride dimer. Preferably, catalyst (C2) is bis(benzonitrile)palladium(II) dichloride. More preferably, catalyst (C2) is used in combination with a phosphine ligand (L), most preferably phosphine ligand (L) is 2-dicyclohexylphosphino-2',4',6'-triisopropylbiphenyl.

Preferably, in this embodiment of the first aspect, solvent (S6) is selected from the group consisting of tetrahydrofuran, dioxane, N,N-dimethylformamide and acetonitrile. Most preferably, solvent (S6) is acetonitrile.

Further preferred within this embodiment is that base (B2) is selected from the group consisting of sodium carbonate, cesium carbonate, potassium carbonate, sodium phosphate, potassium phosphate, lithium carbonate, triethylamine and N,N-diisopropylethylamine. Most preferably, base (B2) is cesium carbonate.

Within this embodiment, the compound of Formula (5), or a salt thereof, is preferably prepared by reacting, in the presence of a solvent (S5) and an activator (Ac2), a compound of Formula (7) with a compound of Formula (6).

Preferably, the activator (Ac2) is a Lewis acid of the Formula $MY_n$ wherein M is a metal selected from the group consisting of aluminum, bismuth, copper, indium, scandium, ytterbium and zinc; Y is selected from the group consisting of trifluoromethanesulfonate and halide; and n is the valency of the metal M. Most preferably, activator (Ac2) is copper (II) triflate.

Further preferred within this embodiment is that solvent (S5) is selected from the group consisting of methyl t-butyl ether, tetrahydrofuran, ethyl acetate, ethanol N,N-dimethylformamide, toluene and acetonitrile. Most preferably, solvent (S5) is toluene.

Within this embodiment, the compound of Formula (7), or a salt thereof, is preferably prepared by a process comprising:
(i) reacting, in the presence of a solvent (S1), the compound of Formula (12) with a compound of $P^a$-$LG^1$ to afford a compound of Formula (11);
(ii) reducing, in the presence of a solvent (S2) and a reductant, the compound of Formula (11) to afford a compound of Formula (10) or a salt thereof;
(iii) reacting, in the presence of a solvent (S3), a compound of Formula (10) and a compound of Formula (9) to afford a compound of Formula (8); and
(iv) deprotecting the compound of Formula (8) to provide the compound of Formula (7).

In further preferred embodiments, X in the compounds of Formulas (8), (10), (11) and (12) is halide, and is most preferably X is bromide; $P^a$-$LG^1$ is preferably selected from the group consisting of N-tert-butoxycarbonylimidazole, 2-(tert-butoxycarbonyloxyimino)-2-phenylacetonitrile, 2-(tert-butoxycarbonylthio)-4,6-dimethylpyrimidine, 1-tert-butoxycarbonyl-1,2,4-triazole, tert-butyl phenyl carbonate, N-(tert-butoxycarbonyloxy)phthalimide, tert-butyl 2,4,5-trichlorophenyl carbonate and di-tert-butyl dicarbonate; and $P^a$ is preferably a tert-butoxycarbonyl group.

In further preferred embodiments, the reductant is hydrogen gas and the reduction is conducted in the presence of catalyst (C1) that is a platinum on carbon catalyst; G in the compound of Formula (9) is $LG^2$, and most preferably, is chloride; and the deprotection comprises acidolysis with an acid (A1), which is preferably trifluoroacetic acid.

In a second aspect of the invention, there is provided a compound of Formula (3):

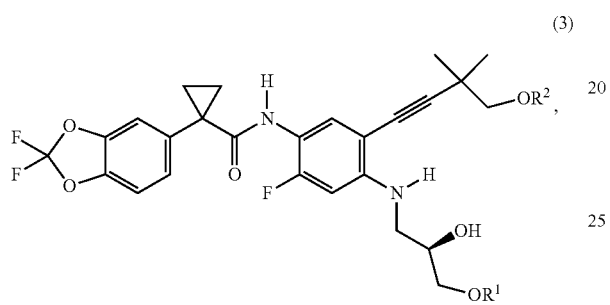

(3)

or a salt thereof,
wherein
$R^1$ is H or $P^1$;
$R^2$ is H or $P^2$; and
$P^1$ and $P^2$ are hydroxyl protecting groups that may be the same or different.

In a preferred embodiment of the second aspect, $R^1$ is $P^1$; $R^2$ is $P^2$; $P^1$ and $P^2$ are $CR^aR^bR^c$ groups that may be the same or different; $R^a$, $R^b$ and $R^c$ are independently selected from the group consisting of H, an unsubstituted alkyl group having 1 to 10 carbon atoms, a substituted alkyl group having 1 to 10 carbon atoms in the alkyl portion, an unsubstituted aryl group having 6 to 14 ring carbon atoms, and a substituted aryl group having 6 to 14 ring carbon atoms; and at least one of the groups $R^a$, $R^b$ and $R^c$ is a substituted or unsubstituted aryl group having 6 to 14 ring carbon atoms. Most preferably, $R^1$ and $R^2$ are both benzyl.

In a third aspect of the invention, there is provided a compound of Formula (5):

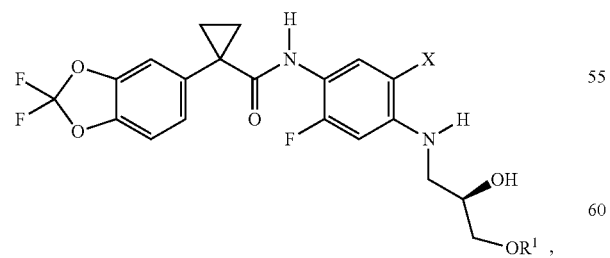

(5)

or a salt thereof,
wherein
X is halide or trifluoromethanesulfonate;
$R^1$ is H or $P^1$; and $P^1$ is a hydroxyl protecting group.

In a preferred embodiment of the third aspect, X is bromide.

In a further preferred embodiment of the third aspect, $R^1$ is $P^1$; $R^2$ is $P^2$; $P^1$ and $P^2$ are $CR^aR^bR^c$ groups that may be the same or different; $R^a$, $R^b$ and $R^c$ are independently selected from the group consisting of H, an unsubstituted alkyl group having 1 to 10 carbon atoms, a substituted alkyl group having 1 to 10 carbon atoms in the alkyl portion, an unsubstituted aryl group having 6 to 14 ring carbon atoms, and a substituted aryl group having 6 to 14 ring carbon atoms; and at least one of the groups $R^a$, $R^b$ and $R^c$ is a substituted or unsubstituted aryl group having 6 to 14 ring carbon atoms. Most preferably, $R^1$ is benzyl.

In a fourth aspect of the invention, there is provided a compound of Formula (7):

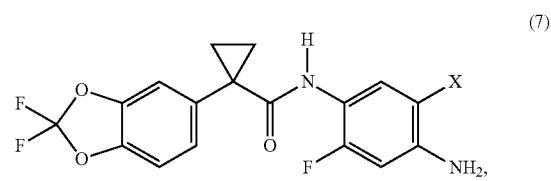

(7)

or a salt thereof,
wherein
X is halide or trifluoromethanesulfonate.

In a preferred embodiment of the fourth aspect, X is bromide.

In a fifth aspect of the invention, there is provided a compound of Formula (8):

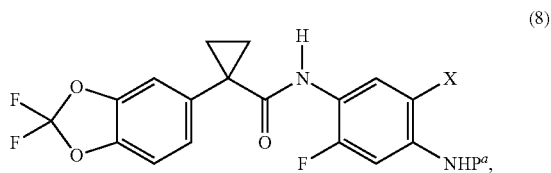

(8)

wherein
X is halide or trifluoromethanesulfonate; and $P^a$ is an amino protecting group.

In a preferred embodiment of the fifth aspect, X is bromide.

In a further preferred embodiment of the fifth aspect, $P^a$ is selected from the group consisting of substituted or unsubstituted alkyloxycarbonyl groups; substituted or unsubstituted arylalkyloxycarbonyl groups; substituted or unsubstituted alkylcarbonyl groups; and substituted or unsubstituted arylalkylcarbonyl groups. Most preferably, $P^a$ is a tert-butoxycarbonyl group.

In a sixth aspect of the invention, there is provided a compound of Formula (10):

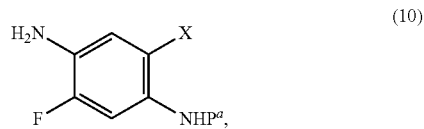

(10)

wherein

X is halide or trifluoromethanesulfonate; and $P^a$ is an amino protecting group.

In a preferred embodiment of the sixth aspect, X is bromide.

In a further preferred embodiment of the sixth aspect, $P^a$ is selected from the group consisting of substituted or unsubstituted alkyloxycarbonyl groups; substituted or unsubstituted arylalkyloxycarbonyl groups; substituted or unsubstituted alkylcarbonyl groups; and substituted or unsubstituted arylalkylcarbonyl groups. Most preferably, $P^a$ is a tert-butoxycarbonyl group.

In a seventh aspect of the invention, there is provided a compound of Formula (11):

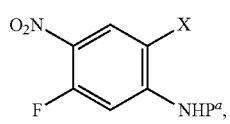

(11)

wherein

X is halide or trifluoromethanesulfonate; and $P^a$ is an amino protecting group.

In a preferred embodiment of the seventh aspect, X is bromide.

In a further preferred embodiment of the seventh aspect, $P^a$ is selected from the group consisting of substituted or unsubstituted alkyloxycarbonyl groups; substituted or unsubstituted arylalkyloxycarbonyl groups; substituted or unsubstituted alkylcarbonyl groups; and substituted or unsubstituted arylalkylcarbonyl groups. Most preferably, $P^a$ is a tert-butoxycarbonyl group.

DETAILED DESCRIPTION

The processes of the present invention provide improvements in the preparation of Tezacaftor (1) over known processes, including provision of several solid isolatable intermediates in good yields under mild reaction conditions, thereby providing processes that are more amenable to industrial application.

As used herein, the term "aliphatic", alone or as part of another substituent, means a straight chain, branched chain or non-aromatic cyclic hydrocarbon radical, or a combination thereof, which may be fully saturated, or mono- or polyunsaturated, and can include di- and multivalent radicals, having from 1 to 10 carbons. Preferably, an aliphatic group has from 1 to 5 carbons. Examples of preferred saturated hydrocarbon radicals include methyl, ethyl, n-propyl, iso-propyl, n-butyl, t-butyl, iso-butyl, and sec-butyl. An unsaturated hydrocarbon radical is one having one or more double bonds or triple bonds. Examples of preferred unsaturated hydrocarbon radicals include vinyl, 2-propenyl, crotyl, 2-isopentenyl, 2-(butadienyl), 2,4-pentadienyl, 3-(1,4-pentadienyl), norbornenyl, ethynyl, 1-propynyl, 2-propynyl, and 3-butynyl.

As used herein, the term "alkyl", alone or as part of another substituent, means, unless otherwise stated, a straight or branched chain, saturated hydrocarbon radical having 1 to 10 carbon atoms. Examples of preferred alkyl groups include methyl, ethyl, n-propyl, iso-propyl, n-butyl, t-butyl, iso-butyl, sec-butyl, n-pentyl, 2,2-dimethylpropyl, n-hexyl, 2-methylpentyl, n-heptyl, n-octyl, 2-methylheptyl, 3-methylheptyl, n-nonyl, 2-methyloctyl and n-decyl. Particularly preferred alkyl groups include methyl, ethyl, n-propyl, iso-propyl, n-butyl, t-butyl, iso-butyl and sec-butyl.

As used herein, the term "aryl", alone or as part of another substituent, means a polyunsaturated, aromatic, hydrocarbon radical which can comprise one, two or three rings, which are fused together or linked covalently, having a total of 6 to 14 ring carbon atoms. Examples of preferred aryl groups include phenyl, 4-biphenyl, 9-fluorenyl, 1-naphthyl, 2-naphthyl, 2-anthryl and 9-anthryl. Particularly preferred aryl groups include phenyl, 1-naphthyl, 2-naphthyl, 2-anthryl and 9-anthryl.

As used herein, the term "substituted" refers to the replacement of one or more hydrogen atoms with a substituent selected from the group consisting of: alkyl, OR", halogen, CN, $NO_2$ and $CF_3$. A substituted group may be mono-substituted or polysubstituted. As used herein, each R" may be selected, independently, from the group consisting of hydrogen and alkyl groups. Preferred examples of substituent groups on substituted aliphatic and aryl groups include methoxy, methyl, nitro, fluoride and chloride.

As used herein, the terms "wt %" refers to weight percent, and is used to express weight part/weight total as a percentage.

As used herein, "room temperature" generally refers to a temperature of 20-25° C.

As used herein, the term "about" means "close to", and that variation from the exact value that follows the term is within amounts that a person of skill in the art would understand to be reasonable. For example, when the term "about" is used with respect to temperature, a variation of ±5° C. is generally acceptable when carrying out the processes of the present invention. When used with respect to mole equivalents, a variation of ±0.1 moles is generally acceptable.

In one embodiment of the present invention, Tezacaftor (1) and intermediates useful in the preparation thereof may be prepared by the process as set out in Scheme 3. Exemplary reagents and conditions for these processes are described herein.

In the processes and compounds of the invention, X is selected from the group consisting of halide and trifluoromethanesulfonate ('triflate' or 'OTf'). Preferably, X is halide selected from the group consisting of chloride, bromide and iodide, and is most preferably bromide.

In the processes and compounds of the invention, $P^a$ is an amino protecting group. Preferably, $P^a$ is selected from the group consisting of substituted or unsubstituted alkyloxycarbonyl groups such as methoxycarbonyl, tert-butoxycarbonyl ('BOC'), 2,2,2-trichloroethoxycarbonyl and 2-trimethylsilylethoxycarbonyl; substituted or unsubstituted arylalkyloxycarbonyl groups such as benzyloxycarbonyl ('CBz'), p-nitrobenzyloxycarbonyl and diphenylmethoxycarbonyl; substituted or unsubstituted alkylcarbonyl groups such as methylcarbonyl ('Ac') and chloromethylcarbonyl; and substituted or unsubstituted arylalkylcarbonyl groups such as benzylcarbonyl ('Bz'). More preferably, $P^a$ is tert-butoxycarbonyl (BOC) or methylcarbonyl (Ac), most preferably, $P^a$ is tert-butoxycarbonyl (BOC).

In the processes and compounds of the invention, $R^1$ is selected from the group consisting of H and $P^1$, and $R^2$ is selected from the group consisting of H and $P^2$. $R^1$ and $R^2$ are can be the same or different. Preferably, $R^1$ and $R^2$ are $P^1$ and $P^2$ groups, respectively.

In the processes and compounds of the invention, $R^{1'}$ is selected from the group consisting of H and $P^1$ and $R^{2'}$ is selected from the group consisting of H and $P^2$. At least one of $R^{1'}$ and $R^{2'}$ is a hydroxyl protecting group $P^1$ or $P^2$, respectively. Preferably, $R^{1'}$ and $R^{2'}$ are $P^1$ and $P^2$ groups, respectively.

$P^1$ and $P^2$ are hydroxyl protecting groups that may be the same or different. Preferably $P^1$ and $P^2$ are $CR^aR^bR^c$ groups wherein $R^a$, $R^b$ and $R^c$ are independently selected from the group consisting of H, an unsubstituted alkyl group having 1 to 10 carbon atoms, a substituted alkyl group having 1 to 10 carbon atoms in the alkyl portion, an unsubstituted aryl having 6 to 14 ring carbon atoms, and a substituted aryl having 6 to 14 ring carbon atoms, wherein at least one of the groups $R^a$, $R^b$ and $R^c$ is a substituted or unsubstituted aryl group having 6 to 14 ring carbon atoms. Preferably, one of $R^a$, $R^b$ and $R^c$ is a substituted or unsubstituted aryl group having 6 to 14 carbon atoms and the remaining groups are each H.

Preferably, when $R^a$, $R^b$ or $R^c$ is an aryl group, the aryl group is selected from the group consisting of phenyl, 1-naphthyl, 2-naphthyl, 2-anthryl and 9-anthryl, and is most preferably phenyl. Substituted aryl groups are preferably substituted with one or more substituents selected from the group consisting of methyl, methoxy and halogen. Most preferably the substituents are selected from methyl and methoxy.

Most preferably, each of $P^1$ and $P^2$ is benzyl.

In another embodiment of the present invention, there is provided a process for the preparation of the compound of Formula (11):

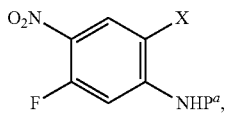

(11)

comprising reacting, in the presence of a solvent (S1), a compound of Formula (12):

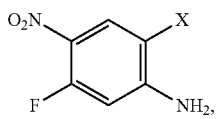

(12)

with a compound $P^a$-$LG^1$,
wherein
X is selected from the group consisting of halide and trifluoromethanesulfonate;
$P^a$ is an amino protecting group; and
$LG^1$ is a leaving group.

$LG^1$ is a leaving group, preferably selected from the group consisting of halogen, N-imidazole, oxyimino-2-phenylacetonitrile, 2-thio-4,6-dimethylpyrimidine, 1,2,4-triazole, phenol, N-hydroxyphthalimide, 2,4,5-trichlorophenol and tert-butyl carbonic acid. Most preferably, $LG^1$ is tert-butyl carbonic acid, and the corresponding compound $P^a$-$LG^1$ is di-tert-butyl dicarbonate ('BOC$_2$O').

The reaction of the compound of Formula (12) and the compound $P^a$-$LG^1$ is conducted in the presence of a solvent (S1). Solvent (S1) is preferably selected from the group consisting of halogenated hydrocarbons, ethers, esters, ketones, hydrocarbons, amides, sulfoxides, alcohols, water and mixtures thereof. More preferably, solvent (S1) is selected from the group consisting of methyl t-butyl ether, tetrahydrofuran, dioxane, ethyl acetate, acetone, acetonitrile, toluene, N,N-dimethylformamide, dimethyl sulfoxide, ethanol, water and mixtures thereof. Most preferably, solvent (S1) is dichloromethane.

The reaction of the compound of Formula (12) and the compound $P^a$-$LG^1$ may be conducted at any suitable temperature, and is preferably conducted at a temperature between about 0° C. and about 50° C., more preferably between about 20° C. and about 30° C.

Compounds of Formula (12) where X is halide are commercially available. Alternatively, the compound of Formula (12) may be prepared by any desired method including, for example, by reacting the 2-amino-4-fluoro-5-nitrophenol with a trifluoromethylsulfonylating agent, such as trifluoromethanesulfonic acid anhydride or trifluoromethanesulfonyl chloride.

In another embodiment of the present invention, there is provided a process for the preparation of the compound of Formula (10):

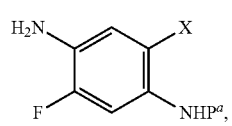

(10)

comprising reducing, in the presence of a solvent (S2) and a reductant, the compound of Formula (11):

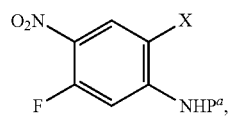

(11)

or a salt thereof,
wherein
X is selected from the group consisting of halide and trifluoromethanesulfonate; and
$P^a$ is an amino protecting group.

The reduction of the compound of Formula (11) is conducted in the presence of a reductant. Preferably, the reductant is selected from the group consisting of a hydrogen source, iron, tin(II) chloride, titanium(III) chloride and zinc. More preferably, the reductant is a hydrogen source selected from the group consisting of hydrogen gas and a hydrogen transfer reagent. The hydrogen transfer reagent selected from the group consisting of cyclohexadiene, tetralin, and formic acid derivatives. Preferably, the formic acid derivative is selected from the group consisting of sodium formate, ammonium formate, triethyl ammonium formate, and formic acid. Most preferably, the reductant is hydrogen gas.

The reduction of the compound of Formula (11) may be conducted in the presence of a catalyst (C1). Preferably, catalyst (C1) is a transition metal catalyst, and is preferably selected from the group consisting of platinum, sulfide platinum, Raney nickel, nickel and platinum(IV) oxide. The transition metal may be finely dispersed solids or adsorbed on an inert support such as carbon or alumina. Catalyst (C1) may be wet or dry. Most preferably, catalyst (C1) is 5 wt % platinum on carbon ('Pt/C'). The catalyst loading may be from about 0.1 wt % to about 20 wt % catalyst (C1) with respect to the weight of the compound of Formula (11).

Preferably, the catalyst loading is 5 wt % catalyst (C1) with respect to the weight of the compound of Formula (11).

The reduction of the compound of Formula (11) may be conducted at any suitable temperature, and is preferably conducted at a temperature between about 0° C. and about 50° C., more preferably between about 20° C. and about 30° C.

In another embodiment of the present invention, there is provided a process for the preparation of the compound of Formula (8):

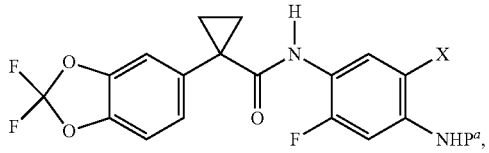
(8)

comprising reacting, in the presence of a solvent (S3), a compound of Formula (10):

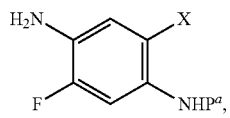
(10)

and a compound of Formula (9):

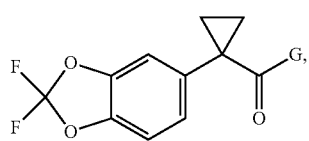
(9)

wherein
P$^a$ is an amino protecting group;
G is selected from the group consisting of OH and LG$^2$; and
LG$^2$ is a leaving group.

In the compound of Formula (9), G is selected from the group consisting of OH and LG$^2$, wherein LG$^2$ is a leaving group. Preferably, G is LG$^2$. Preferably, LG$^2$ is selected from the group consisting of halide and G$^1$, wherein G$^1$ is selected from the group consisting of OR$^3$ and A;
A is selected from the group consisting of:

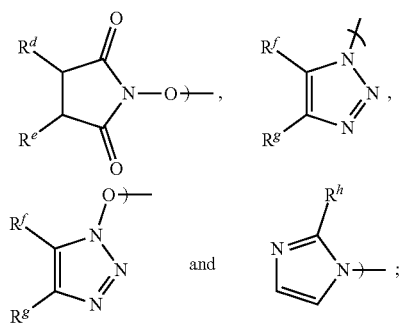

R$^d$ and R$^e$ are either (a) hydrogen, or (b) R$^f$ and R$^g$;
R$^f$ and R$^g$, taken together with the carbon atoms to which they are bonded, form a ring selected from the group consisting of a substituted or unsubstituted aryl group having 6 to 10 ring carbon atoms, a substituted or unsubstituted heteroaryl group having 5 to 9 carbon atoms and at least one heteroatom selected from S, N and O, and a substituted or unsubstituted aliphatic group having 1 to 10 carbon atoms;
R$^h$ is hydrogen or methyl; and
R$^3$ is selected from the group consisting of a substituted or unsubstituted aliphatic group having 1 to 10 carbon atoms, a substituted or unsubstituted aryl group having 6 to 10 ring carbon atoms, and a substituted or unsubstituted arylalkyl group having 6 to 10 ring carbon atoms and 1 to 3 alkyl carbon atoms.

Preferably, when LG$^2$ is a halide, the halide is chloride.

Preferably, when R$^3$ is an aliphatic group, the aliphatic group is selected from the group consisting of methyl, ethyl, n-propyl, isopropyl, n-butyl, t-butyl, isobutyl, and sec-butyl. More preferably, the aliphatic group is methyl or ethyl, and most preferably, the aliphatic group is methyl. Substituted aliphatic groups are preferably substituted with methoxy.

Preferably, when R$^3$ is an aryl group, the aryl group is selected from the group consisting of phenyl, 1-naphthyl, 2-naphthyl and 4-biphenyl, and is most preferably phenyl. Substituted aryl groups are preferably substituted with one or more substituents selected halogen and NO$_2$, and most preferably from chloride, fluoride and NO$_2$.

Preferably, when R$^3$ is an arylalkyl group, the arylalkyl group is selected from benzyl and phenethyl. Substituted arylalkyl groups are preferably substituted with one or more substituents selected from the group consisting of methyl, methoxy, halogen and NO$_2$. Most preferably, the substituents are selected from halogen and NO$_2$.

Preferably, when G$^1$ is A: R$^d$ and R$^e$ are each hydrogen, and A is N-hydroxysuccinimidyl; R$^f$ and R$^g$ taken together with the carbon atoms to which they are bonded form a phenyl ring, and A is benzotriazolyl or N-hydroxybenzotriazolyl; or R$^h$ is hydrogen, and A is imidazolyl. Most preferably, A is N-hydroxysuccinimidyl.

Most preferably, LG$^2$ is chloride.

When G is OH, the reaction of the compound of Formula (9) and the compound of Formula (10) is preferably conducted in the presence of an activating agent (Ac1). Preferably, the activating agent (Ac1) is selected from the group consisting of halogenating agents, carbodiimides, uronium reagents and carbonyldiimidazoles.

When the activating agent (Ac1) is a halogenating agent, it is preferably selected from the group consisting of thionyl chloride, phosphorous trichloride and phosphorous pentachloride. When used, the carbodiimide is preferably used in combination with an additive such as 1-hydroxy-7-azabenzotriazole (HOAt) or 1-hydroxy-1H-benzotriazole (HOBt). Preferably, the carbodiimide is selected from the group consisting of N,N'-dicyclohexylcarbodiimide (DCC), N,N'-diisopropylcarbodiimide (DIC), N-(3-dimethylaminopropyl)-N'-ethylcarbodiimide (EDC) and N-(3-dimethylaminopropyl)-N'-ethylcarbodiimide hydrochloride (EDC HCl). When used, the uronium reagent is preferably selected from the group consisting of O-(7-azabenzotriazol-1-yl)-1,1,3,3-tetramethyluronium hexafluorophosphate (HATU) and O-(benzotriazol-1-yl)-1,1,3,3-tetramethyluroniumhexafluorophosphate (HBTU). When used, the carbonyldiimidazole is preferably selected from the group consisting of 1,1'-carbonyldiimidazole (CDI) and 1,1'-carbonylbis(2-methylimidazole). Most preferably, the activating agent (Ac1) is a halogenating agent, and is preferably thionyl chloride.

The compound of Formula (9) wherein G is LG² may be prepared by treatment of the corresponding acid of Formula (9), wherein G is OH, with an activating agent (Ac1), or any alternative method desired. In the reaction of the compound of Formula (9) and the compound of Formula (10), when G is LG², the compound of Formula (9) may be used in isolated form or it may be generated from the corresponding acid (wherein G is OH) and used in situ without isolation.

The reaction of the compound of Formula (9) and the compound of Formula (10) is conducted in the presence of a solvent (S3). Solvent (S3) is preferably selected from the group consisting of halogenated hydrocarbons, ethers, esters, alcohols, aromatic hydrocarbons and nitriles. More preferably, solvent (S3) is selected from the group consisting of dichloromethane, methyl t-butyl ether, tetrahydrofuran, ethyl acetate, ethanol, toluene and acetonitrile. Most preferably, solvent (S3) is dichloromethane.

The reaction of the compound of Formula (9) and the compound of Formula (10) may be conducted in the presence of a base (B1). Base (B1) may be any base capable of neutralizing acid by-products from the reaction of the compound of Formula (9) and the compound of Formula (10). Base (B1) is preferably selected from the group consisting of tertiary amines, metal carbonates and metal bicarbonates. Preferably, base (B1) is selected from the group consisting of sodium carbonate, sodium bicarbonate, potassium carbonate, potassium bicarbonate, lithium carbonate, triethylamine and N,N-diisopropylethylamine. Most preferably, base (B1) is triethylamine.

In another embodiment of the present invention, there is provided a process for the preparation of the compound of Formula (7):

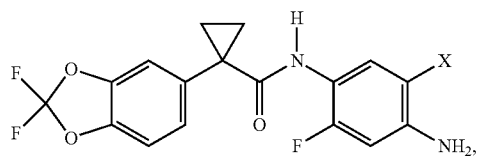

(7)

or a salt thereof, comprising, deprotecting a compound of Formula (8):

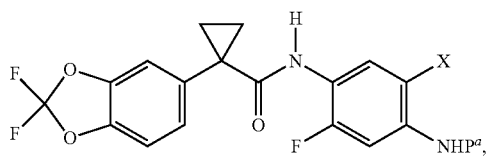

(8)

wherein
X is selected from the group consisting of halide and trifluoromethanesulfonate; and
P^a is an amino protecting group.

In the deprotection of the compound of Formula (8), that is, removal of the amino protecting group (P^a), suitable conditions for cleavage of protecting groups from an amine may be employed. For example, suitable methods may be found in Greene, T. W.; Wuts, P. G. M. *Protective Groups in Organic Synthesis*; Fourth edition; Wiley: New York, 2007. When the protecting group is a carbamate-type or amide-type protecting group (for example, P^a is selected from the group consisting of a substituted or unsubstituted alkyloxycarbonyl group, aryalkyloxycarbonyl group, alkylcarbonyl group and arylalkylcarbonyl group), deprotection of the compound of Formula (8) to produce the compound of Formula (7) is preferably conducted by acidolysis with an acid (A1).

In the deprotection of the compound of Formula (8) by acidolysis, acid (A1) is preferably selected from the group consisting of trifluoroacetic acid, methanesulfonic acid, p-toluenesulfonic acid, camphorsulfonic acid, trifluoromethanesulfonic acid and hydrogen chloride. Most preferably, the acid (A1) is trifluoroacetic acid. Acid (A1) may also function as solvent for the deprotection when the acid is a liquid. Alternatively, the deprotection of the compound of Formula (8) may be conducted in the presence of a solvent (S4) selected from the group consisting of chlorinated hydrocarbons, methyl t-butyl ether, tetrahydrofuran, dioxane, ethanol, methanol, N,N-dimethylformamide, toluene and acetonitrile. Preferably, when used, the solvent (S4) is dichloromethane.

The deprotection of the compound of Formula (8) may be conducted at any suitable temperature, and is preferably conducted at a temperature between about 0° C. and about 50° C., more preferably between about 20° C. and about 30° C.

In another embodiment of the present invention, there is provided a process for the preparation of the compound of Formula (5):

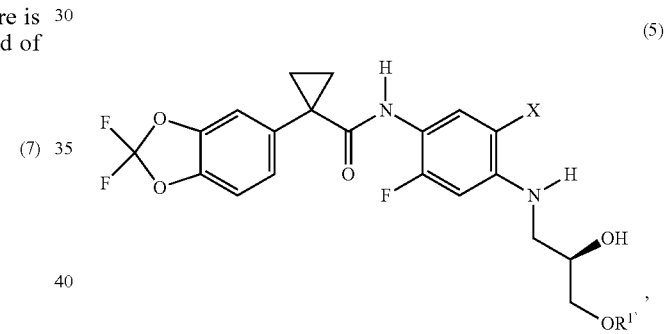

(5)

or a salt thereof, comprising reacting, in the presence of a solvent (S5) and an activator (Ac2), a compound of Formula (7):

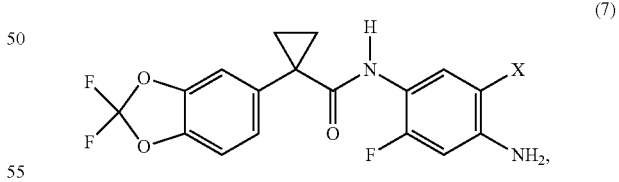

(7)

with a compound of Formula (6):

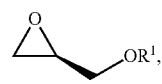

(6)

wherein
X is selected from the group consisting of halide and trifluoromethanesulfonate;

R¹ is selected from the group consisting of H and P¹; and
P¹ is a hydroxyl protecting group.

The reaction of the compound of Formula (6) and the compound of Formula (7) is conducted in the presence of an activator (Ac2). The activator (Ac2) is any suitable agent capable of increasing the reactivity of the reactants. Preferably, activator (Ac2) is a Lewis acid selected from the group consisting of metal perchlorates and compounds of the Formula $MY_n$, wherein M is a metal selected from the group consisting of aluminum, bismuth, copper, indium, scandium, ytterbium and zinc; Y is selected from the group consisting of trifluoromethanesulfonate ('OTf') and halide; and n is 2 or 3, depending on the valency of the metal M. More preferably, the activator (Ac2) is selected from the group consisting of aluminum(III) triflate (Al(OTf)₃), bismuth(III) triflate (Bi(OTf)₃), copper(II) triflate (Cu(OTf)₂), indium (III) triflate (In(OTf)₃), scandium(III) triflate (Sc(OTf)₃), ytterbium(III) triflate (Yb(OTf)₃) and zinc(II) triflate (Zn(OTf)₂). Alcohol solvents, preferably selected from the group consisting of 2-propanol, n-butanol and isoamyl alcohol, can also function as an activator (Ac2). Most preferably, activator (Ac2) is copper(II) triflate (Cu(OTf)₂).

The reaction of the compound of Formula (6) and the compound of Formula (7) is conducted in the presence of a solvent (S5). When the solvent (S5) also functions as the activator (Ac2), it is preferably selected from the group consisting of 2-propanol, n-butanol and isoamyl alcohol. Otherwise, when an alternative activator (Ac2) is used, the solvent (S5) is preferably selected from the group consisting of ethers, esters, amides, aromatic hydrocarbons and nitriles. More preferably, solvent (S5) is selected from the group consisting of methyl t-butyl ether, tetrahydrofuran, ethyl acetate, ethanol N,N-dimethylformamide, toluene and acetonitrile. Most preferably, solvent (S5) is toluene.

The reaction of the compound of Formula (6) and the compound of Formula (7) may be conducted at any suitable temperature, and is preferably conducted at a temperature between about 0° C. and about 50° C., more preferably between about 20° C. and about 30° C.

In another embodiment of the present invention, there is provided a process for the preparation of the compound of Formula (3):

(3)

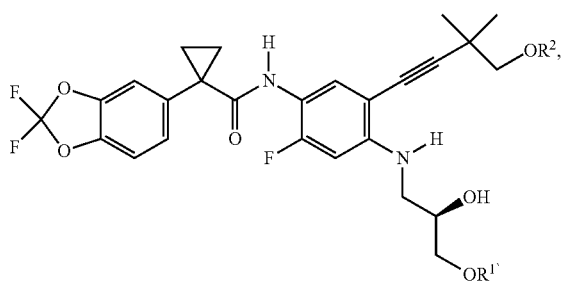

or a salt thereof, comprising reacting, in the presence of a catalyst (C2), a solvent (S6) and a base (B2), a compound of Formula (5):

(5)

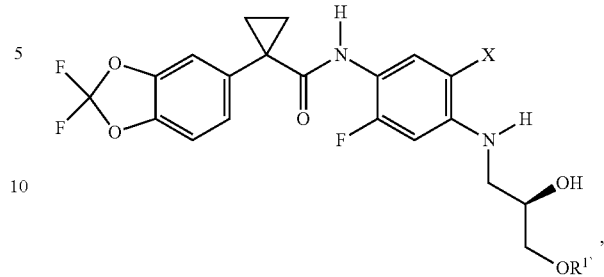

or a salt thereof, with a compound of Formula (4):

(4)

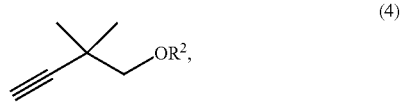

wherein
X is selected from the group consisting of halide and trifluoromethanesulfonate;
R¹ is selected from the group consisting of H and P¹;
R² is selected from the group consisting of H and P²; and
P¹ and P² are hydroxyl protecting groups that may be the same or different.

In the reaction of the compound of Formula (4) and the compound of Formula (5), catalyst (C2) may be any suitable catalyst effective in catalyzing a Sonogashira-type reaction comprising cross-coupling of a terminal alkyne with an aryl electrophile. For example, the catalyst (C2) may be selected from the group consisting of [1,1'-bis(diphenylphosphino)ferrocene]dichloropalladium(II) ([Pd(dppf)Cl₂]), [1,1'-bis(di-tert-butylphoshino)ferrocene]dichloropalladium(I) ([Pd(dtbpf)Cl₂]) tetrakis(triphenylphosphine)palladium(0) (Pd(PPh₃)₄), bromo(tri-tert-butylphosphine)palladium(I) dimer ([Pd(p-Br)(t-Bu₃P)]₂), bis(tri-tert-butylphosphine)palladium(0) ([Pd(tBu₃P)]₂), palladium(II) acetate (Pd(OAc)₂), palladium(II) chloride (PdCl₂), bis(benzonitrile)palladium(II) dichloride ([Pd(PhCN)₂Cl₂]), bis(triphenylphosphine)palladium(II) dichloride ([Pd(PPh₃)₂Cl₂]), bis(acetonitrile)palladium(II) dichloride ([Pd(NCMe)₂Cl₂]), bis[di-tert-butyl(4-dimethylaminophenyl)phosphine]dichloropalladium(II) ([Pd(amphos)Cl₂]), bis[di-tert-butyl(4-dimethylaminophenyl)phosphine]palladium(0) (Pd(amphos)₂), and allylpalladium(II) chloride dimer ([PdCl(C₃H₅)]₂). Preferably, catalyst (C2) is bis(benzonitrile)palladium(II) dichloride ([Pd(PhCN)₂Cl₂]).

Catalyst (C2) may be used in combination with a co-catalyst (CC) and/or a ligand (L). Co-catalyst (CC) is preferably a copper (I) catalyst, and most preferably is copper(I) iodide (CuI). Ligand (L) is preferably selected from the group consisting of 2-dicyclohexylphosphino-2',4',6'-triisopropylbiphenyl ('XPhos'), 2-(dicyclohexylphosphino)-2',6'-isopropoxybiphenyl ('RuPhos'), 4,5-bis(diphenylphosphino)-9,9-dimethylxanthene ('Xantphos'), tricyclohexylphosphine ('PCy₃'), tri-tert-butylphosphine (P(t-Bu)₃), 2,2'-bis(diphenylphosphino)-1,1'-binaphthyl ('BINAP') and 1,1'-bis(diphenylphosphino)ferrocene ('dppf'). Most preferably, ligand (L) is 2-dicyclohexylphosphino-2',4',6'-triisopropylbiphenyl (XPhos). Even more preferably, the catalyst (C2) is a combination of the co-catalyst (CC) copper(I) iodide with the ligand (L) XPhos.

The reaction of the compound of Formula (4) and the compound of Formula (5) is conducted in the presence of a base (B2). The base (B2) is preferably selected from the group consisting of tertiary amines, metal carbonates and metal phosphates. Preferably, base (B2) is selected from the group consisting of sodium carbonate, cesium carbonate, potassium carbonate, sodium phosphate, potassium phosphate, lithium carbonate, triethylamine and N,N-diisopropylethylamine. Most preferably, base (B2) is cesium carbonate.

The reaction of the compound of Formula (4) and the compound of Formula (5) is conducted in the presence of a solvent (S6). Solvent (S6) is preferably selected from the group consisting of ethers, esters, alcohols, amides, aromatic hydrocarbons and nitriles. More preferably, solvent (S6) is selected from the group consisting of tetrahydrofuran, dioxane, N,N-dimethylformamide and acetonitrile. Most preferably, solvent (S6) is acetonitrile.

The reaction of the compound of Formula (4) and the compound of Formula (5) may be conducted at any suitable temperature and is preferably conducted at a temperature between about 20° C. and the boiling point of the reaction mixture. Most preferably, the temperature is between about 70° C. and about 90° C.

In another embodiment of the present invention, there is provided a process for the preparation of Tezacaftor (1):

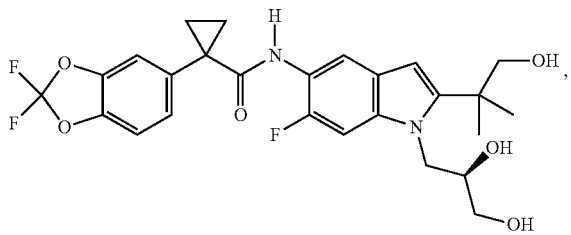

(1)

comprising:
(i) cyclizing, in the presence of a catalyst (C3) and a solvent (S7), a compound of Formula (3):

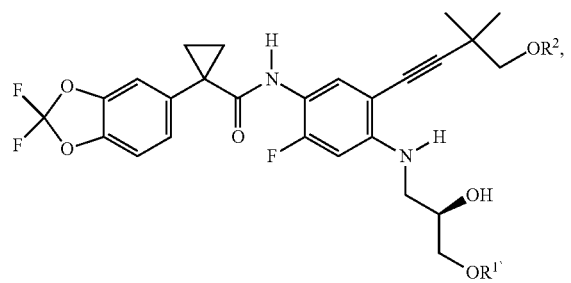

(3)

or a salt thereof, to provide either Tezacaftor (1) when each of $R^1$ and $R^2$ is H, or, when either or both of $R^1$ and $R^2$ is a respective hydroxyl protecting group $P^1$ or $P^2$, a compound of Formula (2):

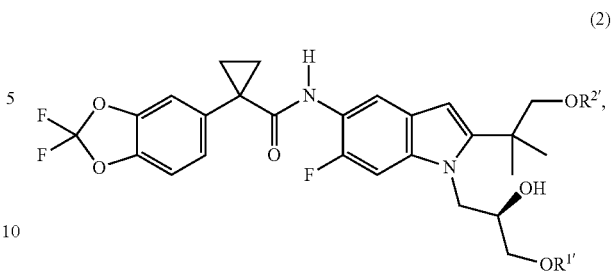

(2)

or a salt thereof,
wherein
$R^1$ is selected from the group consisting of H and $P^1$;
$R^2$ is selected from the group consisting of H and $P^2$;
$R^{1'}$ is selected from the group consisting of H and $P^1$;
$R^{2'}$ is selected from the group consisting of H and $P^2$;
$R^{1'}$ and $R^{2'}$ are not both H; and
$P^1$ and $P^2$ are hydroxyl protecting groups that may be the same or different; and
(ii) when either or both of $R^1$ and $R^2$ is a respective hydroxyl protecting group $P^1$ or $P^2$, deprotecting, in the presence of a solvent (S8), the compound of Formula (2).

The cyclization of the compound of Formula (3) is conducted in the presence of a catalyst (C3). Catalyst (C3) is preferably selected from the group consisting of tetrakis(triphenylphosphine)palladium(0) ($Pd(PPh_3)_4$), palladium (II) chloride ($PdCl_2$), palladium(II) iodide ($PdI_2$), bis(benzonitrile)palladium(II) dichloride ($[Pd(PhCN)_2Cl_2]$), bis(triphenylphosphine)palladium(II) dichloride ($[Pd(PPh_3)_2Cl_2]$), bis(acetonitrile)palladium(II) dichloride ($[Pd(NCMe)_2Cl_2]$), palladium(II) trifluoroacetate ($Pd(TFA)_2$), copper(II) acetate ($Cu(OAc)_2$), and indium(III) bromide ($InBr_3$). Most preferably, catalyst (C3) is palladium(II) chloride ($PdCl_2$).

The cyclization of the compound of Formula (3) is conducted in the presence of a solvent (S7). Solvent (S7) is preferably selected from the group consisting of ethers, alcohols, amides, aromatic hydrocarbons and nitriles. More preferably, solvent (S7) is selected from the group consisting of tetrahydrofuran, ethanol, isopropanol, N,N-dimethylformamide, N-methyl-2-pyrrolidinone, toluene and acetonitrile. Most preferably, solvent (S7) is acetonitrile.

The cyclization of the compound of Formula (3) may be conducted at any suitable temperature, and is preferably conducted at a temperature between about 20° C. and the boiling point of the reaction mixture. Most preferably, the suitable temperature is at or near the boiling point of the reaction mixture.

In the deprotection of the compound of Formula (2) in step (ii), suitable conditions for cleavage of protecting groups from an alcohol may be employed. For example, suitable methods may be found in Greene, T. W.; Wuts, P. G. M. *Protective Groups in Organic Synthesis*; Fourth edition; Wiley: New York, 2007. Preferably, when the protecting group is a benzylic-type protecting group, deprotection is conducted by hydrogenolysis.

Hydrogenolysis may be conducted in the presence of a catalyst (C4) selected from the group consisting of palladium, platinum, rhodium, ruthenium, and Raney-nickel. Catalyst (C4) may be finely dispersed solids or adsorbed on an inert support such as carbon or alumina, and may be wet or dry. Preferably, catalyst (C4) is palladium on carbon (Pd/C). The catalyst loading may be from about 0.1 wt % to about 20 wt % catalyst (C4) with respect to the weight of a compound of Formula (2). Preferably, the catalyst loading is 10 wt % catalyst (C4) with respect to the weight of the compound of Formula (2).

Hydrogenolysis is conducted in the presence of a hydrogen source selected from hydrogen gas or a hydrogen transfer reagent. The hydrogen transfer reagent may be a derivative of formic acid selected from the group consisting of cyclohexadiene, tetralin, and a formic acid derivative. Preferably, the formic acid derivative is selected from the group consisting of sodium formate, ammonium formate, triethyl ammonium formate and formic acid. Preferably, the hydrogen source is sodium formate.

The deprotection of a compound of Formula (2) in step (ii) is conducted in the presence of a solvent (S8) selected from the group consisting of halogenated hydrocarbons, ethers, esters, ketones, hydrocarbons, amides, sulfoxides, alcohols, water and mixtures thereof. Preferably, solvent (S8) is selected from the group consisting of methanol, ethanol, isopropanol, tetrahydrofuran and dioxane. More preferably, solvent (S8) is methanol.

The deprotection of a compound of Formula (2) in step (ii) may be conducted at any suitable temperature, and is preferably conducted at a temperature between about 0° C. and about 50° C., more preferably between about 20° C. and about 30° C.

EXAMPLES

The following examples are illustrative of some of the embodiments of the invention described herein. It will be apparent to the person skilled in the art that various alterations to the described processes in respect of the reactants, reagents and conditions may be made when using the processes of the present invention without departing from the scope or intent thereof.

Example 1: Preparation of tert-butyl (2-bromo-5-fluoro-4-nitrophenyl)carbamate (Compound of Formula (11-A))

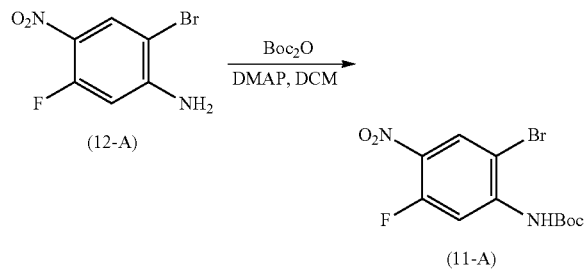

A mixture of the compound of Formula (12-A) (15.00 g, 63.83 mmol) and Boc$_2$O (18.11 g, 82.98 mmol) in dichloromethane (150 mL) was stirred at room temperature for 15 minutes followed by the addition of 4-dimethylaminopyridine ('DMAP') (0.78 g, 6.38 mmol), which resulted in the evolution of a gas. The resulting reaction mixture was stirred at room temperature for 16 hours, following which saturated aqueous ammonium chloride solution (150 mL) was added, resulting in the dissolution of the solids that had formed. The resulting layers were separated, and the organic layer was dried over sodium sulfate and filtered.

Acetonitrile (150 mL) was added to the filtrate and the level of 'di-BOC'-protected material (i.e., the compound of Formula (12) wherein both amino hydrogens are replaced by BOC protecting groups) in the filtrate was estimated by $^1$H-NMR to comprise about 19 mol % of the reaction mixture. The dichloromethane in the filtrate was removed in vacuo, lithium bromide (6.32 g, 7.28 mmol) was added, and the reaction mixture was heated at 65° C. until $^1$H-NMR analysis showed that the di-BOC impurity had been converted to the desired compound of Formula (11-A) (about 5 hours). The reaction mixture was then cooled to room temperature, water (150 mL) and dichloromethane (50 mL) were added, and the resulting layers were separated. The aqueous layer was extracted with dichloromethane (50 mL) and the combined organic layer was concentrated to near dryness. The residue was then dissolved in a minimal quantity of dichloromethane, filtered through a silica plug and the resulting filtrate was concentrated in vacuo to afford the compound of Formula (11-A) as a yellow solid (19.04 g, 56.81 mmol, 89% yield).

$^1$H-NMR of the compound of Formula (11-A) (CDCl$_3$, 400 MHz) δ: 8.35 (1H, d, J=2.3 Hz), 8.31 (1H, d, J=3.9 Hz), 7.32 (1H, br s), 1.56 (9H, s).

Example 2: Preparation of tert-butyl (4-amino-2-bromo-5-fluorophenyl)carbamate (Compound of Formula (10-A))

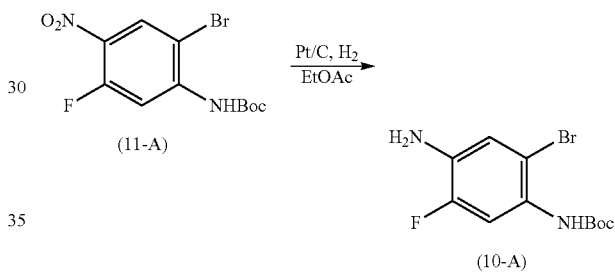

A nitrogen-purged mixture of the compound of Formula (11-A) (15.00 g, 44.76 mmol) and 5% Pt/C (750 mg) in ethyl acetate (150 mL) was placed under a positive pressure of H$_2$ (g) and stirred at room temperature for 16 hours. The reaction mixture was then filtered through diatomaceous earth using ethyl acetate as an eluent to remove the Pt catalyst. $^1$H-NMR analysis of the filtrate showed 23 mol % of unreacted starting material. As a result, the hydrogenation was repeated, following which the ethyl acetate was removed in vacuo to afford the compound of Formula (10-A) as an orange oil (13.53 g, 44.34 mmol, 99% yield).

$^1$H-NMR of the compound of Formula (10-A) (CDCl$_3$, 400 MHz) δ: 7.84 (1H, d, J=12.8 Hz), 6.93 (1H, d, J=8.8 Hz), 6.68 (1H, br s), 3.59 (2H, br s), 1.52 (9H, s).

Example 3: Preparation of tert-butyl (2-bromo-4-{[1-(2,2-difluoro-2H-1,3-benzodioxol-5-yl)cyclopropane-1-carbonyl]amino}-5-fluorophenyl)carbamate (Compound of Formula (8-A))

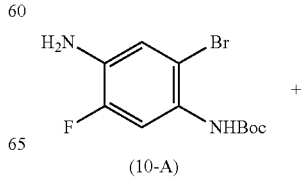

+

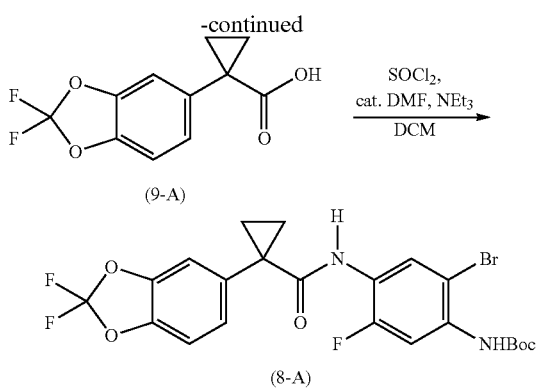

N,N-dimethylformamide (2 drops) was added to a slurry of the compound of Formula (9-A) (11.81 g, 48.77 mmol) in thionyl chloride (10.6 mL, 146.32 mmol) at room temperature. Following stirring at room temperature for about 1.5 hours, the excess thionyl chloride was removed in vacuo from the clear solution, and the resulting material was dissolved in dichloromethane (50 mL) to provide a solution of the corresponding acid chloride. The acid chloride solution was added to a solution of the compound of Formula (10-A) (13.53 g, 44.34 mmol) and triethylamine (20.4 mL, 146.32 mmol) in dichloromethane (50 mL) at room temperature, whereupon a slight exotherm occurred. The resulting mixture was stirred at room temperature for 16 hours, following which, the reaction mixture was quenched with water (100 mL) and the resulting layers were separated. The organic layer was dried over sodium sulfate, filtered and diluted with heptanes (100 mL). The solvent from this solution was reduced in vacuo, resulting in formation of a precipitate, which was collected by filtration, washed with heptanes (50 mL) and dried in vacuo at 40° C. for 2 hours to afford the compound of Formula (8-A) as a brown solid (20.14 g, 38.05 mmol, 86% yield).

$^1$H-NMR of the compound of Formula (8-A) (CDCl$_3$, 400 MHz) δ: 8.46 (d, J=8.0 Hz, 1H), 7.98 (d, J=13.4 Hz, 1H), 7.24-7.19 (m, 2H), 7.18 (br s, 1H), 7.12 (d, 8.2 Hz, 1H), 6.95 (br s, 1H), 1.73 (dd, J=6.8, 3.9 Hz, 2H), 1.51 (s, 9H), 1.17 (dd, J=6.8, 3.9 Hz, 2H).

Example 4: Preparation of N-(4-amino-5-bromo-2-fluorophenyl)-1-(2,2-difluoro-2H-1,3-benzodioxol-5-yl)cyclopropane-1-carboxamide (Compound of Formula (7-A))

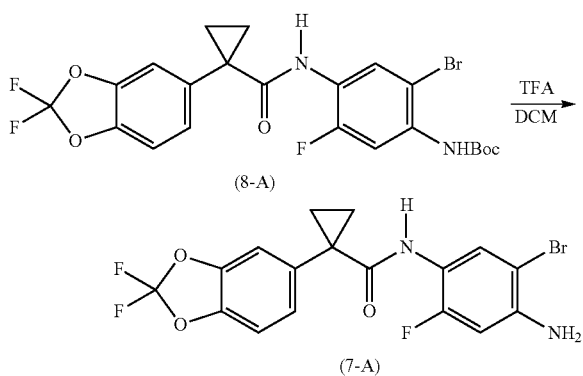 [SMILES: CC(C)(C)OC(=O)Nc1cc(F)c(NC(=O)C2(c3ccc4c(c3)OC(F)(F)O4)CC2)cc1Br ; "(8-A)" ; Nc1cc(F)c(NC(=O)C2(c3ccc4c(c3)OC(F)(F)O4)CC2)cc1Br ; "(7-A)"]

Trifluoroacetic acid (17.4 mL, 226.71 mmol) was added to a solution of the compound of Formula (8-A) (20.00 g, 37.79 mmol) in dichloromethane (100 mL) at room temperature, and the reaction mixture was stirred for 16 hours. After thin-layer chromatography (TLC) (30% ethyl acetate/heptanes) showed full consumption of starting material, the reaction was cooled to 0-5° C. and quenched with saturated aqueous sodium bicarbonate (300 mL). The resulting layers were separated, and the aqueous layer was extracted with dichloromethane (2×50 mL). The organic layers were combined and washed with saturated aqueous sodium bicarbonate (100 mL), water (100 mL) and brine (100 mL). The organic layer was dried over sodium sulfate, filtered and concentrated to dryness to afford the compound of Formula (7-A) as a dark brown solid (16.00 g, 37.28 mmol, 99% yield).

$^1$H-NMR of the compound of Formula (7-A) (CDCl$_3$, 400 MHz) δ: 8.17 (d, J=8.1 Hz, 1H), 7.23-7.20 (m, 2H), 7.10 (d, J=8.1 Hz, 1H), 6.96 (br s, 1H), 6.44 (d, J=12.2 Hz, 1H), 1.72 (dd, J=6.8, 3.9 Hz, 2H), 1.14 (dd, J=6.8, 3.9 Hz, 2H).

Example 5: Preparation of N-(4-{[(2R)-3-(benzyloxy)-2-hydroxypropyl]amino}-5-bromo-2-fluorophenyl)-1-(2,2-difluoro-2H-1,3-benzodioxol-5-yl)cyclopropane-1-carboxamide (Compound of Formula (5-A))

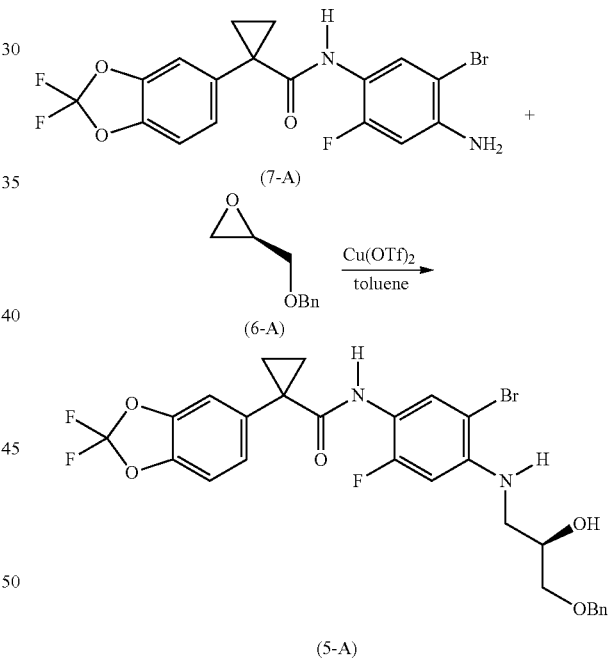

The compound of Formula (6-A) (1.93 g, 11.77 mmol) was added to a mixture of the compound of Formula (7-A) (5.00 g, 11.65 mmol) and Cu(OTf)$_2$ (1.26 g, 3.49 mmol) in toluene (20 mL) at room temperature. After stirring the reaction mixture at room temperature for 17 hours, TLC analysis showed reaction completion. Water (50 mL) and dichloromethane (100 mL) were then added, and the resulting layers were separated. The aqueous layer was extracted with dichloromethane (50 mL), and the combined organic layers were washed with water (100 mL) and brine (100 mL). The organic layer was dried over sodium sulfate, filtered, concentrated to near dryness, and used, as is, in Example 6.

¹H-NMR of the compound of Formula (5-A) (CDCl₃, 400 MHz) δ: 7.38-7.29 (m, 5H), 7.23-7.20 (m, 2H), 7.10 (d, J=8.2 Hz, 1H), 6.93 (br s, 1H), 6.33 (d, J=13.1 Hz, 1H), 4.69 (br s, 1H), 4.56 (s, 2H), 4.05-3.99 (m, 1H), 3.61-3.57 (m, 1H), 3.54-3.51 (m, 1H), 3.27-3.21 (m, 1H), 3.17-3.11 (m, 1H), 2.43 (d, J=5.2 Hz, 1H), 1.72 (dd, J=6.8, 3.9 Hz, 2H), 1.13 (dd, J=6.8, 3.9 Hz, 2H).

Example 6: Preparation of N-[4-{[(2R)-3-(benzyloxy)-2-hydroxypropyl]amino}-5-(3,3-dimethyl-4-phenoxybut-1-yn-1-yl)-2-fluorophenyl]-1-(2,2-difluoro-2H-1,3-benzodioxol-5-yl)cyclopropane-1-carboxamide (Compound of Formula (3-A))

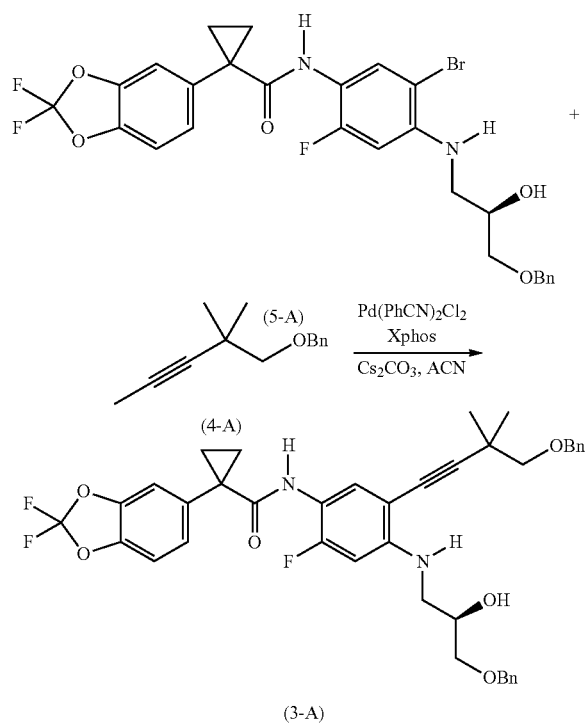

The compound of Formula (4-A) (2.62 g, 12.53 mmol) in degassed acetonitrile (5 mL) was added to a slurry of the compound of Formula (5-A) (used as is from Example 5) (5.72 g, 9.64 mmol), [Pd(PhCN)₂Cl₂] (222 mg, 0.58 mmol), XPhos (551 mg, 1.16 mmol), and cesium carbonate (9.42 g, 28.92 mmol) in degassed acetonitrile (20 mL). The reaction mixture was heated to 80° C. for 2.5 hours whereupon TLC analysis indicated reaction completion. The reaction was cooled to room temperature, charcoal was added, and the mixture was filtered through diatomaceous earth using ethyl acetate as an eluent, followed by concentration of the filtrate to near dryness. The residue was purified by column chromatography (40% ethyl acetate/heptanes) to afford the compound of Formula (3-A) as an orange oil (5.28 g, 7.53 mmol, 65% yield from the compound of Formula (7-A)).

¹H-NMR of the compound of Formula (3-A) (CDCl₃, 300 MHz) δ: 7.89 (d, J=9.2 Hz, 1H), 7.40-7.20 (m, 10H), 7.15-7.10 (m, 1H), 6.88 (s, 1H), 6.23 (d, J=13.4 Hz, 1H), 5.05-4.97 (br s, 1H), 4.59 (s, 2H), 4.52 (s, 2H), 3.91 (br s, 1H), 3.52-3.40 (m, 2H), 3.38 (s, 3H), 3.20-2.97 (m, 2H), 2.33 (br s, 1H), 1.74 (dd, J=6.8, 3.9 Hz, 2H), 1.33-1.25 (br s, 6H), 1.13 (dd, J=6.8, 3.9 Hz, 2H).

Example 7: Preparation of (N-{1-[(2R)-3-(benzyloxy)-2-hydroxypropyl]-2-[1-(benzyloxy)-2-methylpropan-2-yl]-6-fluoro-1H-indol-5-yl}-1-(2,2-difluoro-2H-1,3-benzodioxol-5-yl)cyclopropane-1-carboxamide (Compound of Formula (2-A))

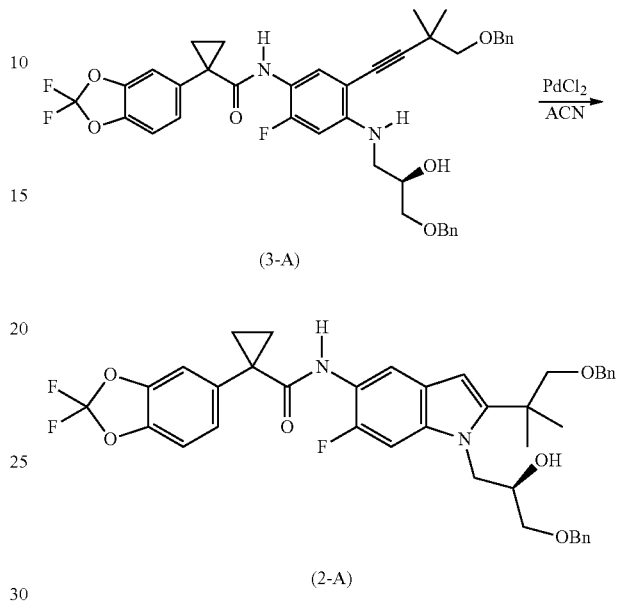

A mixture of the compound of Formula (3-A) (1.24 g, 1.77 mmol) and PdCl₂ (47 mg, 0.27 mmol) in acetonitrile (6 mL) was heated to reflux for 1.5 hours whereupon TLC analysis indicated reaction completion. The reaction mixture was cooled to room temperature and stirred for an additional 16 hours. The mixture was then filtered through diatomaceous earth using ethyl acetate as an eluent, the filtrate was concentrated to near dryness, and the resulting residue was purified by column chromatography (30% ethyl acetate/heptanes) to afford the compound of Formula (2-A) as an orange foam (920 mg, 1.31 mmol, 74% yield).

¹H-NMR of the compound of Formula (2-A) (CDCl₃, 300 MHz) δ: 8.19 (d, J=7.8 Hz, 1H), 7.36-7.19 (m, 9H), 7.14-7.11 (m, 1H), 7.08-7.04 (m, 1H), 6.31 (s, 1H), 4.54-4.46 (m, 4H), 4.29-4.26 (m, 2H), 4.14-4.06 (m, 1H), 3.64 (d, J=9.2 Hz, 1H), 3.51 (d, J=9.2 Hz, 1H), 3.46-3.44 (m, 2H), 2.51 (d, J=5.0 Hz, 1H), 1.75 (dd, J=6.8, 3.9 Hz, 2H), 1.42 (s, 3H), 1.37 (s, 3H), 1.14 (dd, J=6.8, 3.9 Hz, 2H).

Example 8: Preparation of Tezacaftor (1)

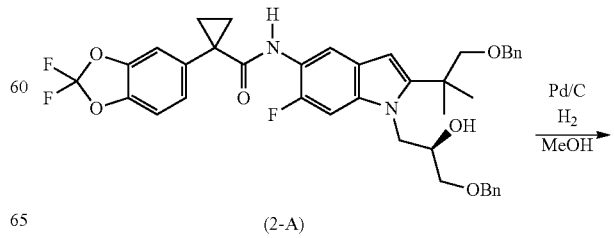

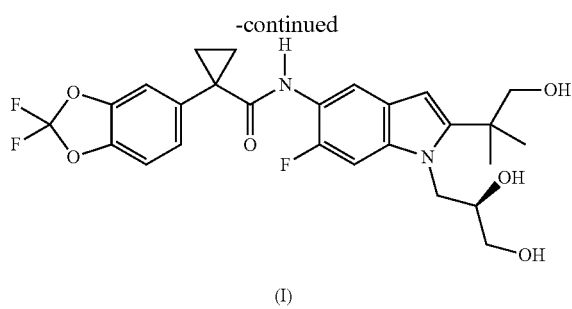

(I)

A mixture of the compound of Formula (2-A) (500 mg, 0.71 mmol) and 5% Pd/C (50 mg) in methanol (5 mL) was stirred under a positive pressure of H₂ (g) at room temperature for 19 hours whereupon TLC analysis indicated reaction completion. The reaction mixture was subsequently filtered through diatomaceous earth using methanol as eluent, and the filtrate was concentrated to near dryness. The isolated yellow foam was dissolved in methyl t-butyl ether (2 mL) and precipitated by addition of heptanes. The precipitated solid was collected by filtration and dried on the filter under aspiration to afford Tezacaftor (1) as an off-white solid (340 mg, 0.65 mmol, 92% yield).

$^1$H-NMR of Tezacaftor (1) (DMSO-d$_6$, 400 MHz) δ: 8.32 (s, 1H), 7.54 (s, 1H), 7.41-7.38 (m, 2H), 7.34-7.31 (m, 2H), 6.22 (s, 1H), 5.03-5.02 (m, 1H), 4.93-4.90 (m, 1H), 4.77-4.75 (m, 1H), 4.42-4.39 (m, 1H), 4.14-4.08 (m, 1H), 3.91 (br s, 1H), 3.64-3.57 (m, 2H), 3.47-3.40 (m, 2H), 3.17-3.11 (m, 1H), 1.48-1.46 (m, 2H), 1.30 (s, 3H), 1.27 (s, 3H), 1.14-1.12 (m, 2H).

What is claimed is:

1. A process for the preparation of Tezacaftor (1):

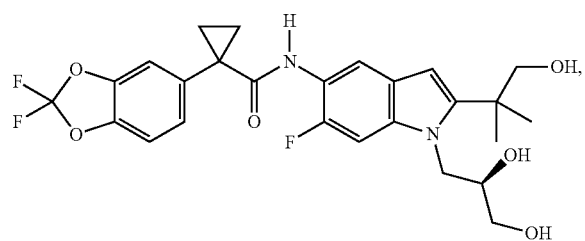

(1)

comprising:
(i) cyclizing, in the presence of a catalyst (C3) and a solvent (S7), a compound of Formula (3):

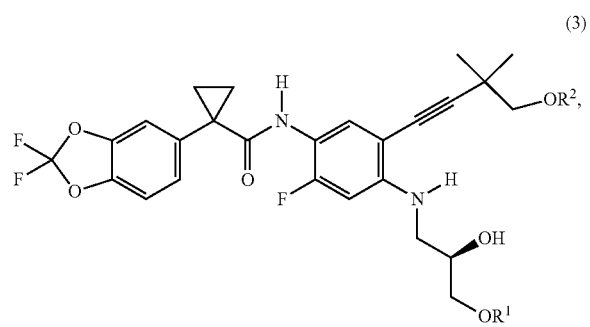

(3)

or a salt thereof,
wherein
R$^1$ is H or P$^1$;
R$^2$ is H or P$^2$; and
P$^1$ and P$^2$ are hydroxyl protecting groups that may be the same or different;
to provide either Tezacaftor (1) when each of R$^1$ and R$^2$ is H, or, a compound of Formula (2):

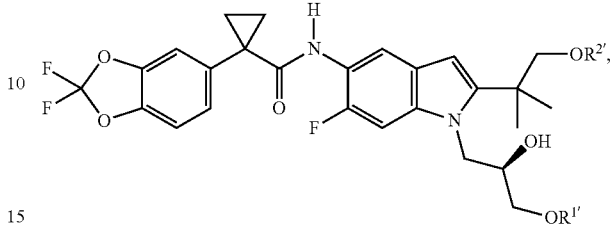

(2)

or a salt thereof,
wherein
R$^{1'}$ is H or P$^1$;
R$^{2'}$ is H or P$^2$;
R$^{1'}$ and R$^{2'}$ are not both H; and
P$^1$ and P$^2$ are hydroxyl protecting groups that may be the same or different; and (ii) when either or both of R$^1$ and R$^2$ in the compound of Formula (3) is a hydroxyl protecting group P$^1$ or P$^2$, deprotecting the compound of Formula (2) in the presence of a solvent (S8) to provide Tezacaftor (1).

2. The process of claim 1, wherein the catalyst (C3) is palladium(II) chloride.

3. The process of claim 1, wherein R$^1$ is P$^1$; R$^2$ is P$^2$; and P$^1$ and P$^2$ are CR$^a$R$^b$R$^c$ groups that may be the same or different, wherein R$^a$, R$^b$ and R$^c$ are independently selected from the group consisting of H, an unsubstituted alkyl group having 1 to 10 carbon atoms, a substituted alkyl group having 1 to 10 carbon atoms in the alkyl portion, an unsubstituted aryl group having 6 to 14 ring carbon atoms, and a substituted aryl group having 6 to 14 ring carbon atoms; wherein at least one of R$^a$, R$^b$ and R$^c$ is a substituted or unsubstituted aryl group having 6 to 14 ring carbon atoms.

4. The process of claim 3, wherein each of P$^1$ and P$^2$ is a benzyl group.

5. The process of claim 3, wherein deprotecting the compound of Formula (2) comprises hydrogenation in the presence of a catalyst (C4) that is palladium on carbon.

6. The process of claim 1, wherein the compound of Formula (3), or a salt thereof, is prepared by reacting, in the presence of a catalyst (C2), a solvent (S6) and a base (B2), a compound of Formula (5):

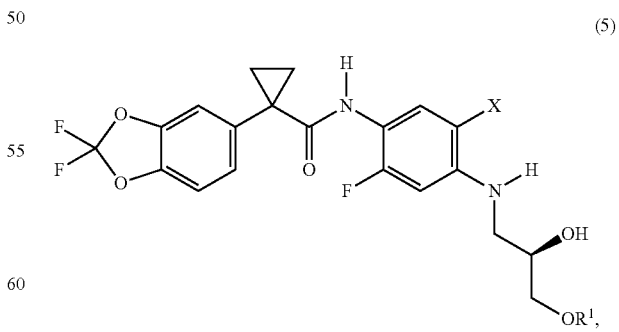

(5)

or a salt thereof,
wherein
X is halide or trifluoromethanesulfonate;
R$^1$ is H or P$^1$; and
P$^1$ is a hydroxyl protecting group.

with a compound of Formula (4):

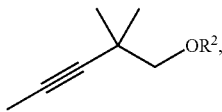
(4)

wherein
R² is H or P²; and
P² is a hydroxyl protecting group.

7. The process of claim 6, wherein the catalyst (C2) is bis(benzonitrile)palladium(II) dichloride.

8. The process of claim 7, wherein the catalyst (C2) is used in combination with a phosphine ligand (L) that is 2-dicyclohexylphosphino-2',4',6'-triisopropylbiphenyl.

9. The process of claim 6, wherein the compound of Formula (5), or a salt thereof, is prepared by reacting, in the presence of a solvent (S5) and an activator (Ac2), a compound of Formula (7):

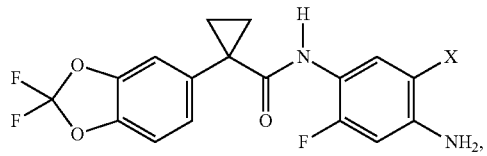
(7)

wherein
X is halide or trifluoromethanesulfonate;
with a compound of Formula (6):

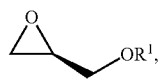
(6)

wherein
R¹ is H or P¹; and
P¹ is a hydroxyl protecting group.

10. The process of claim 9, wherein the activator (Ac2) is a Lewis acid of the Formula $MY_n$, wherein M is a metal selected from the group consisting of aluminum, bismuth, copper, indium, scandium, ytterbium and zinc; Y is trifluoromethanesulfonate or halide; and n is the valency of metal M.

11. The process of claim 10, wherein the activator (Ac2) is copper(II) triflate.

12. The process of claim 9, wherein the compound of Formula (7), or a salt thereof, is prepared by a process comprising:
(i) reacting, in the presence of a solvent (S1), a compound of Formula (12):

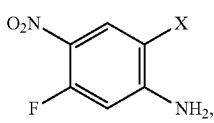
(12)

wherein
X is halide or trifluoromethanesulfonate;
with a compound $P^a$-$LG^1$,
wherein
$P^a$ is an amino protecting group; and
$LG^1$ is a leaving group;
to afford a compound of Formula (11):

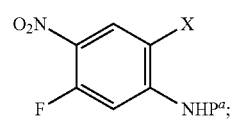
(11)

(ii) reducing, in the presence of a solvent (S2) and a reductant, the compound of Formula (11) to afford a compound of Formula (10):

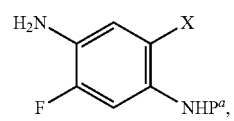
(10)

or a salt thereof,
wherein
X is halide or trifluoromethanesulfonate; and
$P^a$ is an amino protecting group;
(iii) reacting, in the presence of a solvent (S3), a compound of Formula (10) and a compound of Formula (9):

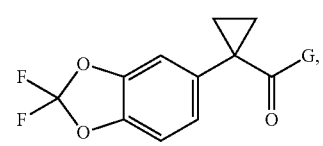
(9)

wherein
G is OH or $LG^2$; and
$LG^2$ is a leaving group,
to afford a compound of Formula (8):

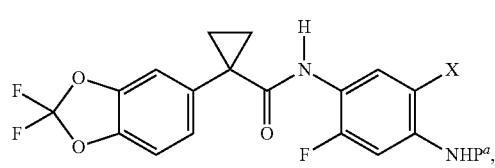
(8)

wherein
X is halide or trifluoromethanesulfonate; and
$P^a$ is an amino protecting group; and
(iv) deprotecting the compound of Formula (8) to provide the compound of Formula (7).

13. The process of claim 12, wherein X is bromide.

14. The process of claim 13, wherein $P^a$ is a tert-butoxycarbonyl group.

15. A compound of Formula (3):

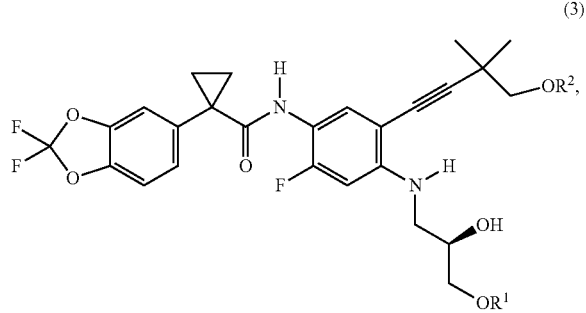

(3)

or a salt thereof,
wherein
R$^1$ is H or P$^1$;
R$^2$ is H or P$^2$; and
P$^1$ and P$^2$ are hydroxyl protecting groups that may be the same or different.

16. The compound of claim 15, wherein R$^1$ is P$^1$; R$^2$ is P$^2$; and P$^1$ and P$^2$ are CR$^a$R$^b$R$^c$ groups that may be the same or different, wherein R$^a$, R$^b$ and R$^c$ are independently selected from the group consisting of H, an unsubstituted alkyl group having 1 to 10 carbon atoms, a substituted alkyl group having 1 to 10 carbon atoms in the alkyl portion, an unsubstituted aryl group having 6 to 14 ring carbon atoms, and a substituted aryl group having 6 to 14 ring carbon atoms; wherein at least one of R$^a$, R$^b$ and R$^c$ is a substituted or unsubstituted aryl group having 6 to 14 ring carbon atoms.

17. The compound of claim 16, wherein R$^1$ and R$^2$ are both benzyl.

18. A compound of Formula (10):

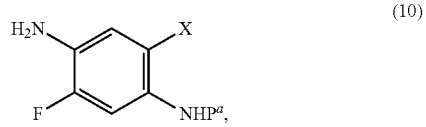

(10)

wherein
X is s halide or trifluoromethanesulfonate; and
P$^a$ is an amino protecting group selected from the group consisting of substituted or unsubstituted alkyloxycarbonyl groups; substituted or unsubstituted arylalkyloxycarbonyl groups; substituted or unsubstituted alkylcarbonyl groups; and substituted or unsubstituted arylalkylcarbonyl groups.

19. The compound of claim 18, wherein X is bromide.

20. The compound of claim 19, wherein P$^a$ is a tert-butoxycarbonyl group.

* * * * *